(12) United States Patent
Ma et al.

(10) Patent No.: US 6,593,301 B1
(45) Date of Patent: Jul. 15, 2003

(54) USE OF STEROIDAL SAPONINS FOR THE PROPHYLAXIS OR TREATMENT OF DEMENTIA, AND NOVEL STEROIDAL SAPONIN COMPOUNDS

(75) Inventors: Baiping Ma, Beijing (CN); Junxing Dong, Beijing (CN); Bingji Wang, Beijing (CN)

(73) Assignee: Institute of Radiation Medicine, Beijing (CN)

( * ) Notice: Subject to any disclaimer, the term of this patent is extended or adjusted under 35 U.S.C. 154(b) by 0 days.

(21) Appl. No.: 09/509,287

(22) PCT Filed: Sep. 28, 1998

(86) PCT No.: PCT/CN98/00204

§ 371 (c)(1),
(2), (4) Date: Jun. 5, 2000

(87) PCT Pub. No.: WO99/16786

PCT Pub. Date: Apr. 8, 1999

(51) Int. Cl.[7] .................. A01N 45/00; A01N 61/00; A01N 43/04
(52) U.S. Cl. .................. 514/26; 514/1; 514/44
(58) Field of Search .................. 514/1, 26, 44

(56) References Cited

FOREIGN PATENT DOCUMENTS

| DE | 4303214 | * | 11/1994 |
| EP | 0054570 A1 | | 3/1981 |
| WO | WO97/31933 | | 9/1997 |

OTHER PUBLICATIONS

Derwent World Patent Index (WPI) abstract for DE 4303214 A1.

* cited by examiner

Primary Examiner—Jezia Riley
(74) Attorney, Agent, or Firm—Senniger, Powers, Leavitt & Roedel

(57) ABSTRACT

The invention relates to the steroidal saponin compounds for the propylaxis or treatment dementia, the new steroidal saponin compounds and the pharmaceutical composition containing the same.

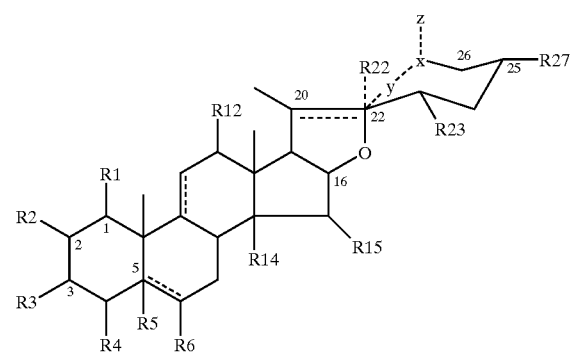

Formula I

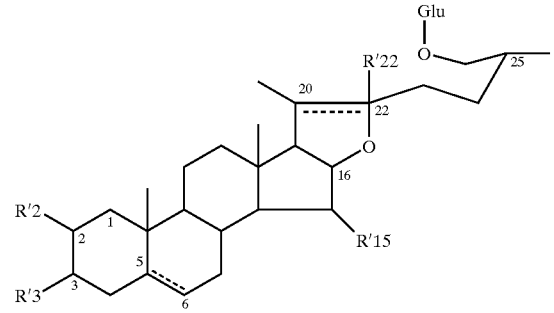

Formula II

15 Claims, 2 Drawing Sheets

Figure 1:
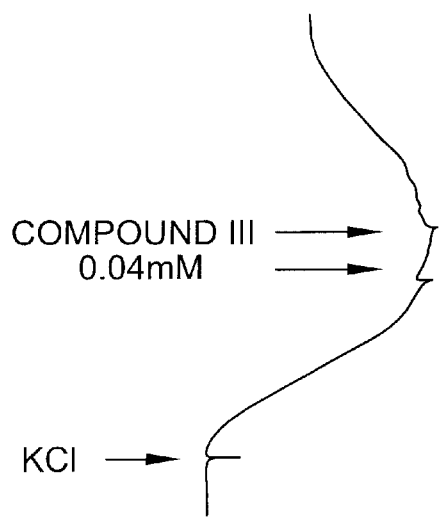

USE OF STEROIDAL SAPONINS FOR THE PROPHYLAXIS OR TREATMENT OF DEMENTIA, AND NOVEL STEROIDAL SAPONIN COMPOUNDS

FIELD OF THE INVENTION

The invention relates to the steroidal saponin compounds for the propylaxis or treatment dementia, the new steroidal saponin compounds and the pharmaceutical composition containing the same.

BACKGROUND

Dementia is a frequently encountered disease in the aged people and also defined by global cognitive decline involving gradual loss of memory, reasoning, judgment, and orientation. It mainly includes Alzheimer's disease (AD), vascular dementia (VD), mixed dementia and some other types. It is reported that incidence of dementia is 3–8% in the elderly over 65, which is as high as 20% in the elderly over 80. Shanghai, China collaborated with the United States to conduct a survey of dementia recently, and the result showed that the incidence of dementia was 4.32% in the aged over 65 in Shanghai. With the improvement of society and elongation of human life span, each country all over the world is getting into aging society and the number of patients suffering dementia will rise remarkably. The dementia has been a medical and social problem to be solved.

Recently, much attention is paid to the discovery and development of drugs for treating dementia. Although there is no definitive treatment or cure for AD, different pharmacological strategies are being actively investigated. At present, cholinesterase inhibitors (tacrine, huperzine A), nootropic agents (hydergin), calcium passage inhibitor (nimodipine) and nerve growth factor represent the available approaches to symptomatic treatment of AD. Development of new effective drugs for treating dementia is therefore of great social importance and economical benefits.

Steroidal saponin is a group of oligosaccharide glycosides derived from spirostane. It is widely distributed in plants including monocotyledon and dicotyledon, especially in Dioscoreaceae, Liliaceae, Scrophulariaceae, Smilacaceae, Agavaceae and so on. For example, steroidal saponins are rich in *Dioscorea nipponica* Makino, *Dioscorea panthaica* Prain et Burk, *Allium sativum L., Anemarrhena asphodeloides Bge., Paris polyphlla, Polygonatum odoratum* (Mill) Drace, *Ophiopogon japonicus, Agave americana L.* and so on. Steroidal saponins are famous for their sapogenins which are precursors for the partial synthesis of steroidal contraceptive and hormones drugs, so sapogenins are more important than themselves. Researchers also found that some steroidal saponins can antineoplasma, decrease blood sugar, accommodate immunity, decrease cholesterol, treat cardiovascular disease and have activity of antisepsis. For example, saponin I and IV from *Paris polyphylla* have cytotoxic effect on $P_{388}$, L-1210 and KB cells. Prototimosaponin AIII and pseudoprototimosaponin AIII from *Anemarrhena asphodeloides Bge*, taken orally exhibited hypoglycemic effects in a dose-dependent manner in streptozotocin- and alloxan-diabetic mice. Saponins from *Ophiopogon japonicus* showed immunostimulating activity on mice. The scholars in the former Soviet Union discovered that some steroidal saponins could lower cholesterol, and the activity of spirostanol saponin is higher than that of furostanol saponin. Steroidal saponin has activity of antisepsis as it can form complex with the cholesterol in bacterial cell membrane. Water soluble saponins from *Dioscorea zingiberensis* Wright can relieve cardiac angina, accommodate metabolism and treat coronary heart disease.

OBJECT OF THE INVENTION

The object of the invention is to provide a new class of pharmaceuticals for the propyhylaxis or treatment of dementia with high effective and low side action.

SUMMARY OF THE INVENTION

Through wide and deep study, the inventors have unexpectedly discovered that the steroidal saponins of formula I can dilate the cerebral basilar artery, improve cerebral circulation and metabolism, up-regulate the number of nicotinic receptor significantly, promote the proliferation of nerve cells, and scavenge free radicals. Noticeably, in the cultural experiments of two cell lines, SY-SH5Y and M10, it is discovered that the compounds of this invention can effectively up-regulate the number of nAChRs and the potency is similar to that of nicotine. Moreover, the effect is concentration-dependent. As a result, the compounds of formula I can be used to prevent or treat dementia. Completeness of this invention is based on above discoveries.

The first aspect of this invention relates to a use of steroidal saponin compounds of formula I and their stereoisomers for the propylaxis or treatment of dementia, Formula I

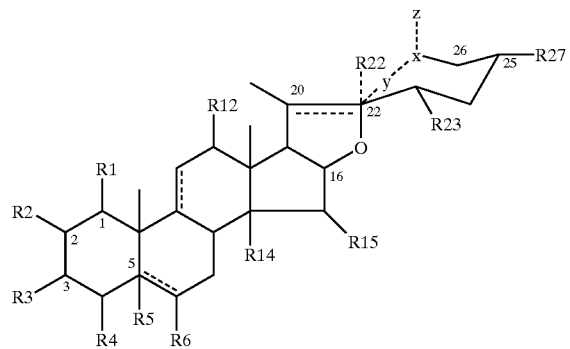

Wherein $R_1$ is hydrogen, —OH, —O-Xyl, —O-Ara-Rha, —O-Fuc-Rha, —O-Ara-Rha,

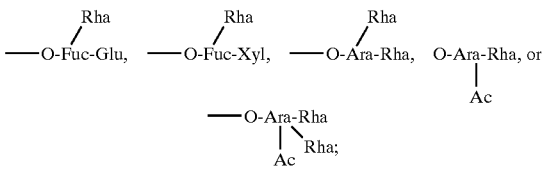

$R_2$ is hydrogen, —OH, —O-Fuc, —O-Rha, or —O-Glu;
$R_3$ is —OH, —OCOCH$_3$, —OCOC$_{15}$H$_{31}$, or oxo(=O), or
—O-Gal,
—O-Glu,
—O-Gal-Glu,
—O-Glu-Glu,
—O-Glu-Ara,
—O-Fuc-Glu,
—O-Rha,
—O-Rha-Glu,
—O-Glu-Glu-Glu,

```
       Glu
      /
  —O-Glu-Rha,
      \
       Glu
```

—O-Glu-Rha,
—O-Man-Glu,
—O-Gal-Glu-Glu,

```
       Rha
      /
  —O-Glu-Glu,
       Rha
      /
  —O-Glu-Rha,
       Glu
      /
  —O-Glu-Glu,
       Rha
      /
  —O-Gal-Gal,
       xyl
      /
  —O-Glu-Ara,
       Rha
      /
  —O-Gal-Glu,
       Rha
      /
  —O-xyl-Rha,
       Glu
      /
  —O-Glu-Ara,
       Rha
      /
  —O-Glu-xyl,
       Rha
      /
  —O-Gal-xyl,
       Glu
      /
  —O-Gal-Glu-xyl,
       Gal
      /
  —O-Gal-Glu-Xyl,
       Glu
      /
  —O-Gal-Glu-Glu,
       xyl-Rha
      /
  —O-Gal-Glu-Glu,
       xyl-xyl
      /
  O-Gal-Glu-Glu,
       Glu
      /
  O-Gal-Glu-Glu-Rha,
       Glu-Ac
      /
  O-Gal-Glu-Glu,
       Glu
      /
  —O-Gal-Glu-Glu,
       |
       Ac
       Glu
      /
  —O-Gal-Glu-xyl-Glu,
       Glu-Rha
      /
  —O-Gal-Glu-Glu-xyl,
       Glu-Glu
      /
  —O-Gal-Glu-xyl-Glu,
  —O-Gal-Glu-Gal,
       Api
      /
  —O-Glu-Rha,
```

```
       Rha
      /
  —O-Gal-Glu-Glu,
       Gal
      /
  —O-Glu-Glu-xyl,
       Glu
      /
  —O-Gal-Glu-xyl-Rha,
       xyl
      /
  —O-Gal-Glu-xyl,
       |
       Rha
       Glu
      /
  —O-Glu-Glu-Gal
       \
       xyl,
       Glu
      /
  —O-Gal-Glu-Glu-Api,
       Glu
      /
  —O-Gal-Glu-xyl-Api;
```

$R_4$ is hydrogen, —OH, or —$OSO_3Na$, $R_5$ is hydrogen, hydroxy, —O-Glu, or is absent, $R_6$ is hydrogen, OH, oxo(=O), —O-Qui-Rha, or —O-Qui-Xyl;

$R_{12}$ is hydrogen, —OH, or oxo(=O);

$R_{14}$ is hydrogen, or —OH;

$R_{15}$ is hydrogen, or —OH;

$R_{22}$ is hydroxy, or $O(CH_2)_nCH_3$, n=0~3, or is absent, $R_{23}$ is hydrogen, or —OH;

$R_{27}$ is —$CH_3$, —$CH_2OH$, or =$CH_2$;

X is O, or NH;

==== denotes a single bond or a double bond,

Y is a direct bond or is absent,

Z is Glu or is absent, provided that a compound of formula I wherein $R_1=R_2=R_4=R_6=R_{12}=R_{14}=R_{15}=R_{23}=H$, $R_3=\beta$-OH, $R_5=\beta$-H, X=O, ==== is a single bond, Y is a direct bond, $R_{22}$ is absent, Z is absent, $R_{27}$ is —$CH_3$, $C_{25}$ is (S) configuration, is not included.

The second aspect of this invention relates to the novel steroidal saponins represented by formula II

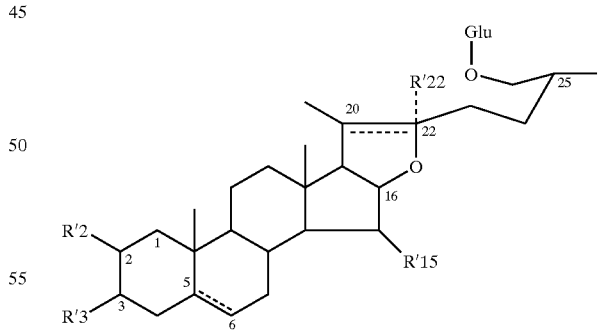

Formula II

Wherein the dotted line between positions 5 and 6 deotes no double bond, 5-position is $\beta H$ $C_{25}$ is S-configuration $R'_{15}$ is hydrogen $R'_2$ is $\alpha$-OH or $\beta$-OH $R'_3$ is —O-$Gal^2Glu$, —O-$Gal^2Glu^2Glu$,
—O-$Gal^4Glu^2Glu$,
—O-$Gal^4Glu^3Glu$,

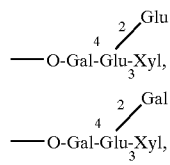

$R'_{22}$ is OH, or $O(CH_2)_nCH_3$, n=0~3, or $R'_{22}$ is absent, at the same time the dotted line between positions 20 and 22 denotes double bond; or $R'_2$ is hydrogen $R'_3$ is —O-Gal-Glu, the dotted line between positions 5 and 6 denotes no double bond, 5-position is βH, $C_{25}$ is (S) configuration, $R'_{15}$ is α-OH or β-OH, $R'_{22}$ is OH, or $O(CH_2)_nCH_3$, n=0–3, or $R'_{22}$ is absent, and at the same time the dotted line between positions 20 and 22 denotes a double bond; or $R'_2$ is hydrogen, the dotted line between positions 5–6 denotes a double bond $R'_{15}$ is hydrogen, $C_{25}$ is R or S configuration, $R'_{22}$ is $O(CH_2)_nCH_3$, n=0–3, or $R'_{22}$ is absent, and at the same time the dotted line between position 20–22 denotes a double bond, $R'_3$ is —O-Gal, —O-Glu, —O-Glu$^2$Rha, —O-Glu$^3$Rha, —O-Glu$^4$Rha, —O-Glu$^4$Glu,

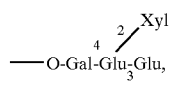

—O-Gal$^4$Glu,

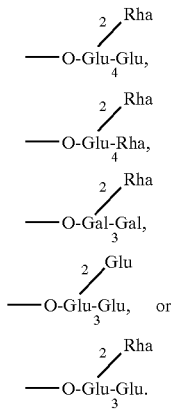

The further aspect of this invention relates to the pharmaceutical composition for the propylaxis or treatment of dementia, which comprises a compound of formula I as active component and pharmaceutically acceptable carrier, excipients, or additives.

The further aspect of this invention relates to the use of a compound of formula I for the preparation of pharmaceuticals for the propylaxis or treatment of dementia.

The last aspect of this invention relates to the method of the propylaxis or treatment of dementia, which include administering a propylaxis or treatment effective amount of a compound of formula I or the pharmaceutical composition containing the same to host which need the propylaxis or treatment of dementia.

DETAILED DESCRIPTION OF INVENTION

Illustration of Figures:

FIG. 1 displays the inhibitory effect of compound III of the present invention on the contraction of rat aorta caused by KCl.

Figure 2:
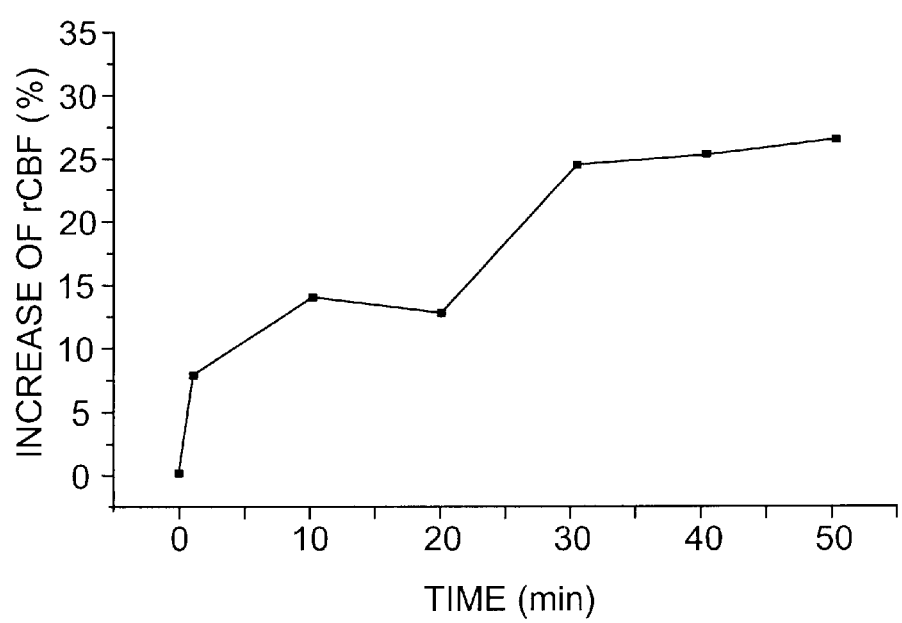

FIG. 2 shows the influence of compound III of the present invention on cerebral blood flow in rats.

Figure 3:
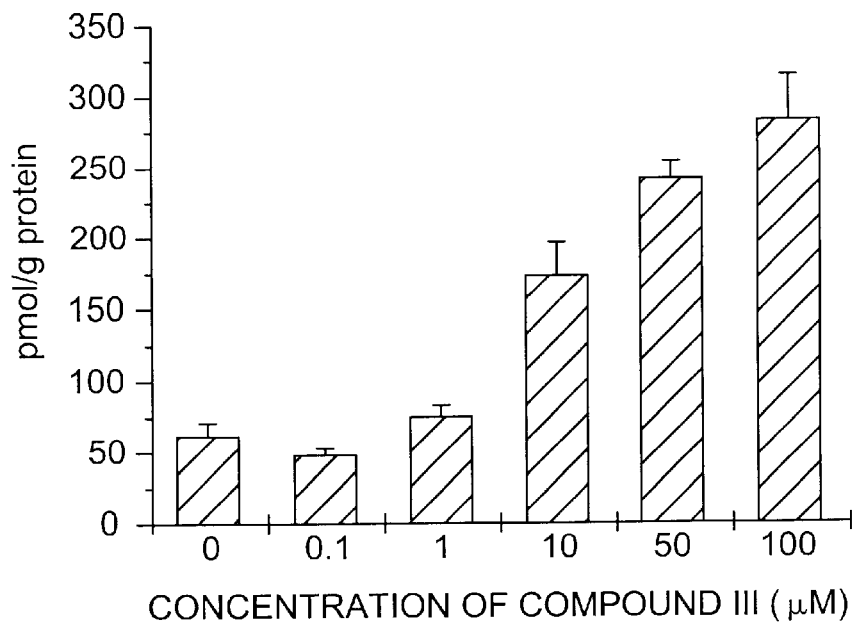

FIG. 3 demonstrates the action of Compound III of the present invention on nicotinic receptors—[$^3$H]nicotine specific binding to M10 cells treated with Compound III.

Figure 4:
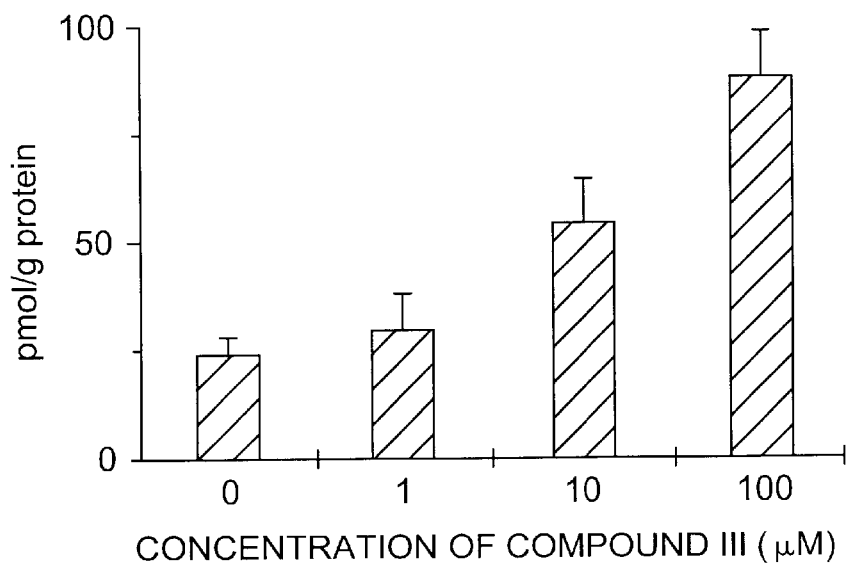

FIG. 4 demonstrates the action of Compound III of the present invention on nicotinic receptors—[$^3$H]epilbatidine specific binding to SY-SH5Y cells treated with Compound III.

This invention first relates to a use of compounds of formula I and their stereoisomers for the propylaxis or treatment of dementia, Formula I

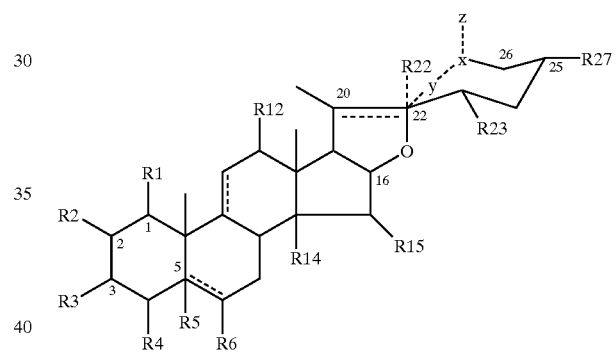

Wherein $R_1$ is hydrogen, —OH, —O-β-Xyl, —O-Ara-Rha, —O-Fuc-Rha, —O-Ara-Rha,

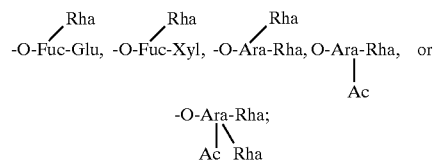

$R_2$ is hydrogen, —OH, —O-Fuc, —O-Rha, or —O-Glu;

$R_3$ is —OH, —OCOCH$_3$, —OCOC$_{15}$H$_{31}$, or oxo(=O), or

—O-Gal,

—O-Glu,

—O-Gal-Glu,

—O-Glu-Glu,

—O-Glu-Ara,

—O-Fuc-Glu,

—O-Rha,

—O-Rha-Glu,

—O-Glu-Glu-Glu,

—O-Glu-Rha,
—O-Man-Glu,
—O-Gal-Glu-Glu,

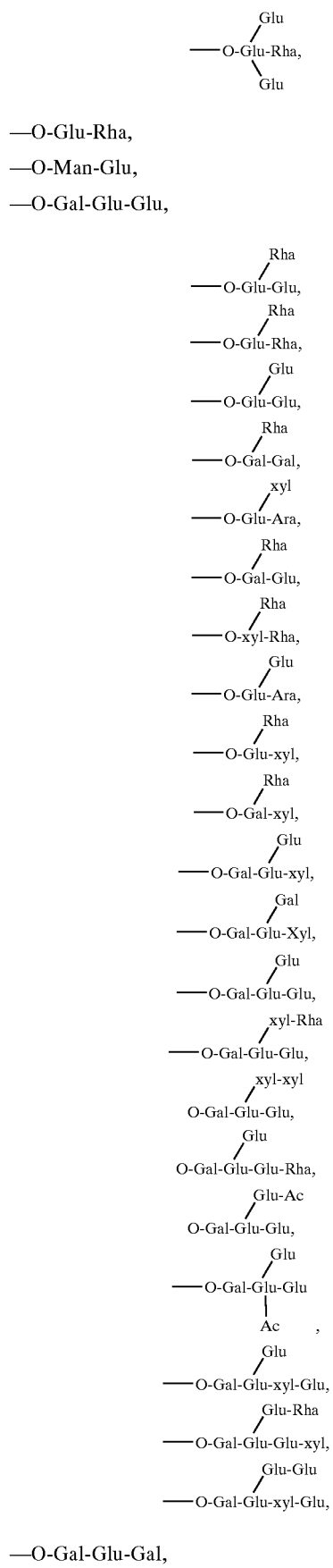

—O-Gal-Glu-Gal,

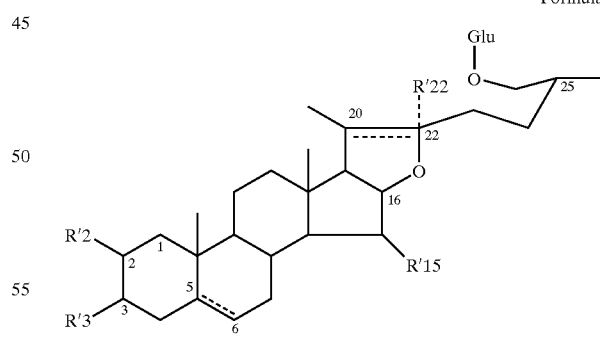

$R_4$ is hydrogen, —OH, or —OSO$_3$Na,
$R_5$ is hydrogen, hydroxy, —O-Glu, or is absent,
$R_6$ is hydrogen, OH, oxo(=O), —O-Qui-Rha, or —O-Qui-Xyl;
$R_{12}$ is hydrogen, —OH, or oxo(=O);
$R_{14}$ is hydrogen, or —OH;
$R_{15}$ is hydrogen, or —OH;
$R_{22}$ is hydroxy, or O(CH$_2$)$_n$CH$_3$, n=0~3, or is absent
$R_{23}$ is hydrogen, or —OH;
$R_{27}$ is —CH$_3$, —CH$_2$OH, or =CH$_2$;
X is O, or NH;
=== denotes a single bond or a double bond,
Y is a direct bond or is absent,
Z is Glu or is absent,
provided that a compound of formula I wherein $R_1=R_2=R_4=R_6=R_{12}=R_{14}=R_{15}=R_{23}$=H, $R_3$=β-OH, $R_5$=β-H, X=O, === is a single bond, Y is a direct bond, $R_{22}$ is absent, Z is absent, $R_{27}$ is —CH$_3$, $C_{25}$ is (S) configuration, is not included.

The further aspect of this invention relates to the novel steroidal saponins represented by formula II Formula II Wherein
the dotted line between positions 5 and 6 deotes no double bond, 5-position is βH,
$C_{25}$ is S-configuration,
$R'_{15}$ is hydrogen,
$R'_2$ is α-OH or β-OH,
$R'_3$ is —O-Gal$^2$Glu,
—O-Gal$^2$Glu$^2$Glu,
—O-Gal$^4$Glu$^2$Glu,
—O-Gal$^4$Glu$^3$Glu,

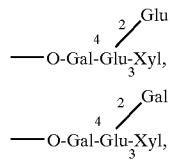

R'$_{22}$ is OH, or O(CH$_2$)$_n$CH$_3$, n=0–3, or R'$_{22}$ is absent, at the same time the dotted line between positions 20 and 22 denotes a double bond; or R'$_2$ is hydrogen R'$_3$ is —O-Gal-Glu, the dotted line between positions 5 and 6 denotes no double bond, 5-position is βH, C$_{25}$ is (S) configuration, R'$_{15}$ is α-OH or β-OH, R'$_{22}$ is OH, or O(CH$_2$)$_n$CH$_3$, n=0–3, or R'$_{22}$ is absent, and at the same time the dotted line between positions 20 and 22 denotes a double bond; or R'$_2$ is hydrogen the dotted line between positions 5–6 denotes a double bond R'$_{15}$ is hydrogen, C$_{25}$ is R or S configuration, R'$_{22}$ is O(CH$_2$)$_n$CH$_3$, n+0–3, or R'$_{22}$ is absent, and at the same time the dotted line between position 20–22 denotes a double bond, R'$_3$ is —O-Gal, —O-Glu, —O-Glu$^2$Rha, —O-Glu$^3$Rha, —O-Glu$^4$Rha, —O-Glu$^4$Glu,

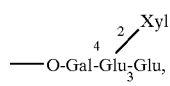

—O-Gal$^4$Glu,

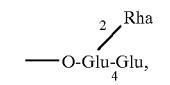

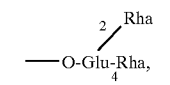

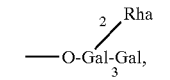

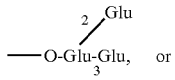 or

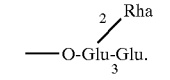

It should be understood that there exists a chiral carbon atom in the compounds of formula I or formula II, thereby the stereo-isomer of compound represented by formula I or formula II is also included in the scope of the invention.

In the formula I or formula II, the abbreviation, is explained below.

Glu: glucose,

Gal: galactose,

Rha: rhamnose,

Xyl: xylose,

Ara: arabinose,

Fuc: fucose,

Man: mannose,

Qui: quinovose,

Apl: aplose.

According to the present invention, the preferred is a compound of formula I wherein R$_1$=R$_2$=R$_4$=R$_6$=R$_{12}$=R$_{14}$=R$_{15}$=R$_{23}$=H, R$_3$ is —O-β-Gal$^2$-β-Glu, R$_5$=β-H, R$_{27}$=—CH$_3$, C$_{25}$ is S-configuration, X is O, Z is -β-Glu, Y is absent, R$_{22}$ is absent, the dotted line between position C$_{20}$–C$_{22}$ is a double bond, other === is a single bond.

According to the present invention, the preferred is a compound of formula I wherein R$_1$=R$_2$=R$_4$=R$_6$=R$_{12}$=R$_{14}$=R$_{15}$=R$_{23}$=H, R$_3$ is —O-β-Glu$^2$-β-Glu, R$_5$=β-H, R$_{27}$=—CH$_3$, C$_{25}$ is S-configuration, X is O, Z is -β-Glu, Y is absent, R$_{22}$ is absent, the dotted line between position C$_{20}$–C$_{22}$ is a double bond, other === is a single bond.

According to the present invention, the preferred is a compound of formula I wherein R$_1$=R$_2$=R$_4$=R$_6$=R$_{12}$=R$_{14}$=R$_{15}$=R$_{23}$=H, R$_{22}$ is OH, R$_3$ is —O-β-Gal$^2$-β-Glu, R$_5$=β-H, C$_{25}$ is S-configuration, R$_{27}$=—CH$_3$, X is O, Z is -β-Glu, Y is absent, === is a single bond.

According to the present invention, the preferred is a compound of formula I wherein R$_1$=R$_2$=R$_4$=R$_6$=R$_{12}$=R$_{14}$=R$_{15}$=R$_{23}$=H, R$_{22}$—OCH$_3$, R$_3$ is —O-β-Gal$^2$-β-Glu, R$_5$=βH, C$_{25}$ is S-configuration, R$_{27}$=—CH$_3$, X is O, Z is -β-Glu, Y is absent, === is a single bond.

According to the present invention, the preferred is a compound of formula I wherein R$_1$=R$_2$=R$_4$=R$_6$=R$_{12}$=R$_{14}$=R$_{15}$=R$_{23}$=H, R$_3$ is $$\text{-O-β-Gal}^4\text{-β-Glu}^2\text{-β-Glu}, \quad R_5 = \alpha\text{-H}, R_{22}$$
$$|^3$$
$$\beta\text{-xyl}$$

is absent, R$_{27}$=—CH$_3$, X=O, Y is a direct bond, Z is absent, === is a single bond, C-25 is R-configuration.

According to the present invention, the preferred is a compound of formula I wherein R$_1$=R$_2$=R$_4$=R$_6$=R$_{12}$=R$_{14}$=R$_{15}$=R$_{22}$=R$_{23}$=H, R$_3$ is $$\text{-O-β-Gal-β-Glu-β-Glu}, \quad R_5 = \alpha\text{-H}, R_{22}$$
$$|^3$$
$$\beta\text{-xyl}$$

is absent, R$_{27}$=—CH$_3$, X=O, Y is a direct bond, Z is absent, === is a single bond, C-25 is S-configuration.

According to the present invention, the preferred is a compound of formula I wherein $R_1=R_4=R_6=R_{12}=R_{14}=R_{15}=R_{23}=H$, $R_2=-\alpha\text{-OH}$, $R_3$ is

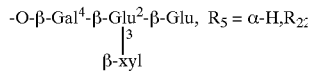

is absent, $R_{27}=-CH_3$, X=0, Y is a direct bond, === is a single bond, Z is absent, C-25 is R-configuration.

According to the present invention, the preferred is a compound of formula I wherein $R_1=R_4=R_6=R_{12}=R_{14}=R_{15}=R_{23}=H$, $R_2=\alpha\text{-OH}$, $R_3$ is

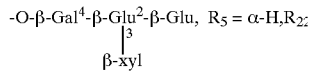

is absent, $R_{27}=-CH_3$, X=0, Y is a direct bond, === is a single bond, Z is absent, C-25 is S-configuration.

According to the present invention, the preferred is a compound of formula I wherein $R_1=R_2=R_4=R_6=R_{12}=R_{14}=R_{15}=R_{23}=H$, $R_3$ is

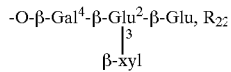

is absent, $R_{27}=-CH_3$, X=0, Y is a direct bond, Z is absent, C-25 is R-configuration, $R_5$ is absent, === at $C_{5-6}$ is a double bond, other === is a single bond.

According to the present invention, the preferred is a compound of formula I wherein $R_1=R_2=R_4=R_6=R_{12}=R_{14}=R_{15}=R_{23}=H$, $R_5$ is absent, $R_{22}$ is absent,

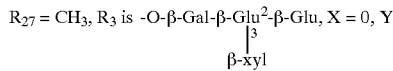

is a direct bond, Z is absent, C-25 is S-configuration, === at $C_{5-6}$ is a double bond, other === is a single bond.

According to the present invention, the preferred is a compound of formula I wherein $R_1=R_2=R_4=R_6=R_{12}=R_{14}=R_{15}=R_{23}=H$, $R_2=-\alpha\text{-OH}$, $R_3$ is

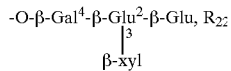

is absent, $R_{27}=-CH_3$, X=0, Y is a direct bond, Z is absent, C-25 is R-configuration, $R_5$ is absent, === at $C_{5-6}$ is a double bond, other === is a single bond.

According to the present invention, the preferred is a compound of formula I wherein $R_1=R_4=R_6=R_{12}=R_{14}=R_{15}=R_{23}=H$, $R_2=\alpha\text{-OH}$, $R_3$ is

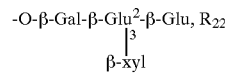

is absent, $R_{27}=-CH_3$, X=0, Y is a direct bond, Z is absent, C-25 is S-configuration, $R_5$ is absent, === at $C_{5-6}$ is a double bond, other === is a single bond.

According to the invention, the preferred compounds of formula I are selected from consisting of:

(25S)-26-0-β-D-glucopyranosyl-22-hydroxy-5β-furost-3β,26-diol-3-0-β-glucopyranosyl(1→2)-β-D-galactopyranoside;

(25S)-26-0-β-D-glucopyranosyl-22-hydroxy-5β-furost-2β,3β,26-triol-3-0-β-D-glucopyranosyl(1→2)-β-D-galactopyranoside;

(25R)-26-0-β-D-glucopyranosyl-22-hydroxy-5-ene-furost-3β,26-diol-3-0-α-L-rhamnopyranosyl(1→2)[β-D-glucopyranosyl(1→3)]-β-D-glucopyranoside;

(25R)-26-0-β-D-glucopyranosyl-22-hydroxy-5-ene-furost-3β,26-diol-3-0-α-L-rhamnopyranosyl(1→2)[α-L-rhamnopyranosyl(1→4)]-β-D-glucopyranoside;

(25R)-26-0-β-D-glucopyranosyl-22-hydroxy-5-ene-furost-3β,26-diol-3-0-β-D-galactopyranosyl(1→2)[β-D-galactopyranosyl(1→3)]-β-D-glucopyranoside;

(25R)-26-0-β-D-glucopyranosyl-22-hydroxy-5-ene-furost-3β,26 diol-3-0-α-L-rhamnopyranosyl(1→2)-β-D-glucopyranoside;

(25S)-26-O-β-D-glucopyranosyl-5β-furost-20(22)-ene-3β,26-diol-3-O-β-D-glucopyranosyl(1→2)-β-D-galactopyranoside;

According to the invention, the preferred compounds of formula II are selected from consisting of:

(25S)-26-O-β-D-glucopyranosyl-22-hydroxy-5β-furost-2β,3β,26-triol-3-O-β-D-glucopyranosyl(1→2)-β-D-galactopyranoside;

(25S)-26-O-β-glucopyranosyl-22-methoxy-5β-furost-2β,3β,26-triol-3-O-β-D-glucopyranosyl(1→2)-β-D-galactopyranoside;

(25S)-26-O-β-D-glucopyranosyl-5β-furost-20(22)-ene-2β,3β,26-triol-3-O-β-D-glucopyranosyl(1→2)-β-galactopyranoside;

(25R)-26-O-β-D-glucopyranosyl-22-hydroxy-5-ene-furost-3β,26diol-3-O-β-D-glucopyranosyl(1→4)-β-D-galactopyranoside;

(25R)-26-O-β-D-glucopyranosyl-22-methoxy-5-ene-furost-3β,26-diol-3-O-β-D-glucopyranosyl(1→4)-β-D-galactopyranoside;

(25R)-26-O-β-D-glucopyranosyl-5-ene-furost-20(22)-ene-3β,26-diol-3-O-β-D-glucopyranosyl(1→4)-β-D-galactopyranoside.

According to the present invention, the pharmaceutical compositions of the present invention comprises the compounds of formula I as active component and pharmaceutically acceptable carrier, excipients, or additives.

According to the present invention, the pharmaceutical compositions of the present invention comprises the compounds of formula II as active component and pharmaceutically acceptable carrier, excipients, or additives.

According the present invention, the present invention further relates to a use of compounds of formula I or stereo-isomer thereof for the manufacture of pharmaceuticals for the propylaxis or treatment of dementia.

According to the present invention, this invention further relates to the methods of the propylaxis or treatment of dementia, which includes administering a propylaxis or treatment effective amount of the compounds of formula I of or the pharmaceutical composition containing the same to hosts which need the propylaxis or treatment of dementia.

In the present invention, the term "dementia" means Alzheimer's disease, vascular dementia, mixed type of dementia and other types of dementia.

In the present invention, the compounds of formula I and formula II may be obtained from plants such as *Anemar-* rhena asphodeloides Bge., Dioscorea panthaica Prain et Burk, *Allium sativum L., Paris polyphlla, Polygonatum odoratum* (Mill) Drace, *Ophiopogon japonicus, Agave americana L. Dioscorea nipponica* Makino, and so on, or prepared by synthesis.

APPLICATION OF INDUSTRY

The compourds represented by the general formula (I) are used for pharmaceuticals as in the forms of usual general pharmaceutical preparations. Said pharmaceutical preparations are formulated by using usually used diluents such as fillers, bulking fillers, binder, wetting agents, disintegrants, surface active agents, lubricants; or excipients. The pharmaceutical preparations can be selected from various administration forms in accordance with the therapeutic purpses. As to typical administration forms, there can be exemplified tablets, pills, powders, liquids, suspensions, emulsions, granules, capsules, suppositories, injection preparations (liquids, suspensions, etc.) and the like. For the purpose of shaping the administration unit form into the tablets, various carriers which are well-known in this field can be widely used. As to the examples of carriers, excipients such as lactose, white sugar, sodium chloride, glucose, urea, starch, calcium carbonate, kaolin, crystalline cellulose, silicic acid and the like; binders such as water, ethanol, propanol, simple syrup, glucose solution, starch solution, gelatin solution, carboxymethyl cellulose, shellac, methyl cellulose, potassium phosphate, polyvinyl-pyrrolidone and the like; disintegrants such as dry starch, sodium alginate, agar-agar powder, laminaran powder, sodium hydrogencarbonate, calcium carbonate, polyoxyethylene sorbitan fatty acid esters, sodium laurylsulfate, monoglyceride of stearic acid, starch, lactose and the like; disintegration inhibitors such as white sugar, stearin, cacao butter, hydrogenated oils and the like; absorption accelerators such as quaternary ammonium salts, sodium laurylsulfate and the like; wetting agents such as glycerin, starch and the like; adsorbents such as starch, lactose, kaolin, bentonite, colloidal silicic acid and the like; lubricants such as refined talc, stearates, boric acid powder, polyethylene glycols and the like can be mentioned. The tablets preparations can be further shaped into tablets coated with usual tablet coating, for example sugar coated tablets, gelatin film coated tablets, tablets coated with enteric coating, tablets coated with film coating, or double layer tablets and multiple layer tablets. For the purpose of shaping the administration unit into pills, various carriers which are well-known in this field can be widely used. As to the examples of carriers, excipients such as glucose, lactose, starch, cacao butter, hydrogenated vegetable oils, kaolin, talc and the like; binders such as powdered acacia, powdered tragacanth, gelatin, ethanol and the like; disintegrants such as laminaran, agar-agar and the like can be exemplified. For the purpose of shaping the administration unit into suppositories, various carriers which are well-known in this field can be widely used. As to the examples of carriers, polyethylene glycols, cacao butter, higer alcohols, esters of higher alcohols, gelatin, semi-synthesized glycerides and the like can be mentioned. For the purpose of shaping the administration unit form into capsules, the compounds of formula I as the effective ingredient is mixed with the above-mentioned various carriers and the mixture thus obtained is placed into hard gelatin capsules or soft capsules. For the purpose of shaping the administration unit into hard gelatin capsules or soft capsules. For the purpose of shaping the administration unit into injection preparations, liquid preparations, emulsion preparations and suspension preparations are sterilized, further these preparations are preferably isotonic to the blood, and the all diluents which are conventionally used in this field can also be used for example, water, ethyl alcohol, macrogols, propylene glycol, ethoxylated isostearyl alcohol polyoxylated isostearyl alcohol, polyoxyethylenesorbitan fatty acid esters can be used. Additionally, for the purpose to prepare isotonic injection solutions, an adequate amount of sodium chloride, glucose or glycerin may be added to the injection preparations, further, usual dissolving additives, buffering agents, local anesthetics and the like may be added. Moreover, if necessary, coloring agents, preservatives, spices, flavors, sweetening agents and others may be added to the pharmaceutical preparations.

The amount of the compounds of formula I as effective ingredient to be contained in the pharmaceutical preparation of the present invention is not specifically restricted and can be suitably selected from a wide range.

Methods for administering the pharmaceutical preparation of the present invention are not restricted, they can be administered in accordance with various forms of preparations, age of the patient, distinguish of sex and other conditions, the degree of the symptom and the like. For example, tablets, pills, liquids, suspensions, emulsions, granules and capsuled are administered orally. While, injection preparations are intravascularly administered, singly or by mixing with common transfusions such as glucose or amino acid solutions, and if necessary, they are singly administered intramuscularly, intracutaneously, subcutaneously or intraperitonealy. Suppositories are administered to the rectum.

Dose of pharmaceutical preparation of the present invention is suitably selected depend on the usage, age of the patient, distinguish of sex and other conditions, and degree of the symptom.

The following examples and pharmacological experiments will demonstrate it in detail, but it does not mean any limitation for this invention.

Rhizoma Anemarrhenae is the rhizome of the *Anemarrhena asphodeloldes Bge.*(Liliaceae). Due to the heart-clearing and fire-purging function and the action of promoting the production of body fluid and nourishing the lung, it has frequent clinical practice. We extracted and purified the steroidal saponins from the Rhizoma Anemarrhenae, elucidated their structures and studied their activities.

EXAMPLE 1

The dried rhizomes of *Anemarrhena asphodeloides Bge.* (3 kg) were refluxed three times with 90% EtOH, concentrated and retrieved EtOH in vacuum, and got 700 g crude extract. The crude extract was dissolved in water, filtered, and got water-soluble fraction and water-insoluble fraction. Water-soluble fraction was concentrated and extracted with n-BuOH. The n-BuOH solution was concentrated and got 90 g extract. It was chromatographied on the silica gel column and eluted with $CHCl_3$—MeOH—$H_2O$ (60:35:10 lower phase). Each fraction was 150 ml, and fraction 54 to fraction 62 with high polarity were combined to recover a subfraction, which was subjected to column chromatography on silica gel again with the lower phase of $CHCl_3$—MeOH—$H_2O$ (first 60:35:10, then 55:35:10). We combined the Fr. 45 to Fr. 48 (each is 100 ml) and got the 1.2 g residue. It was purified with reversed-phase preparative HPLC repeatedly, and lyophilized to get compound I (28.0 mg), compound II (11.8 mg) compound III (57.4mg) and compound IV (20.0 mg) respectively.

Water-insoluble fraction was refluxed with MeOH—CHCl₃ (1:1), and the solution was concentrated to afford a pale extract (38 g), which was subjected to column chromatography on silica gel with the lower phase of CHCl₃—MeOH—H₂O to give 9 fractions (Fr. I–IX). Fr. IV was purified by rechromatography on silica gel with CHCl₃—MeOH—H₂O (60:30:10, lower phase) Fractions with the same TLC profiles were combined to recover thirteen fractions (Fr. 1 to Fr. 13). Among them, Fr. 7 and Fr. 9 were purified by reversed-phase preparative HPLC with a RI detector. The steroial ingredients, tentatively designated as substance V (13.0 mg) and substance VII (11.5 mg), were obtained from Fr. 7 with MeOH—H₂O (90:10) solvent, while substance VI (10.6 mg) and substance VIII (11.7 mg), were from Fr. 9 with MeOH—H₂O (80:20) solvent. Substance V to VIII are four mixtures of a couple of epimers respectively. "a" represents 25R isomer and "b" represents 25S isomer.

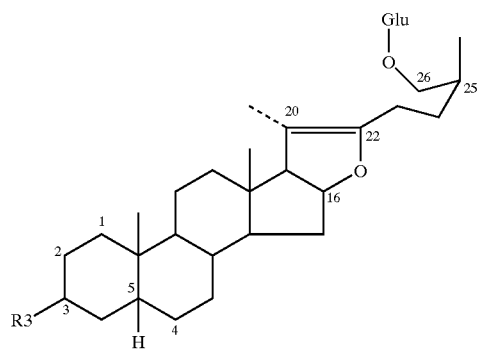

I: R3—O—CuI²—Glu
II: R3—O—CuI¹—Glu

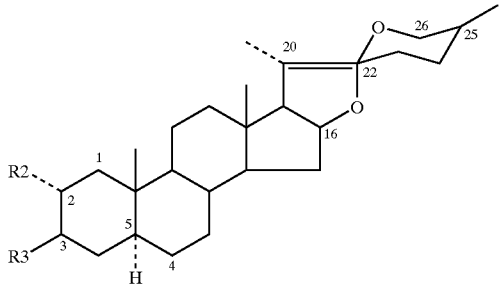

Va: 25R R2—H
Vb: 25S R2—H
Va: 25R R2—OH
Vb: 25S R2—OH

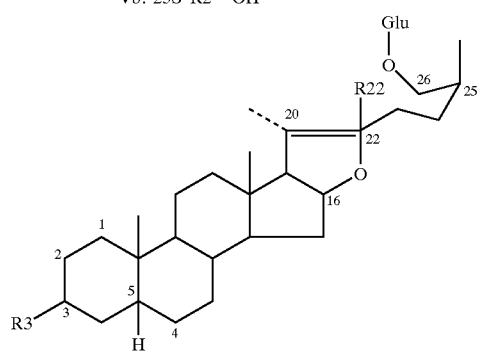

III: R3—O—CuI²—Glu, R22—OH
VI: R3—O—CuI¹—Glu, R22—OCH₃

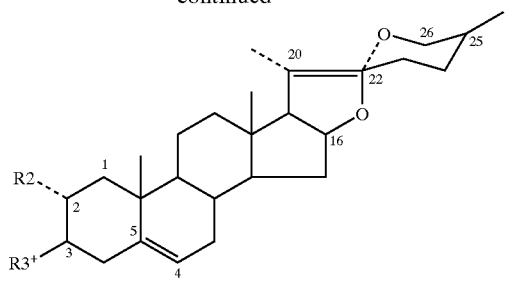

VIIa: 25R R2—H
VIIb: 25S R2—H
VIIIa: 25R R2—OH
VIIIb: 25S R2—OH

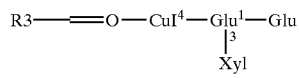

EXAMPLE 2

The dried rhizomes of *Anemarrhena asphodeloides Bge.* (2 kg) were decocted four times with boiling water. The solution was concentrated and precipitated with EtOH (final concentration: 75%). The supernatant was concentrated in vacuum, and then extracted with n-BuOH The n-BuOH solution was concentrated to give 90 g residue. It was chromatographied on the silica gel column and eluted with CHCl₃—MeOH—H₂O repeatedly. The elution was checked by TLC, and the fractions containing compound III were combined to be subjected to column chromatography again on Sephadex LH-20 to get compound III 7.1 g).

Structural Elucidation

Compound I White amorphous powder, mp>226° C. (dec). It is positive to Liebermann-Burchard, Molish reaction, and Ehrlich's reagent. IR $\gamma_{max}$ cm⁻¹: 3368 (OH), 2925, 1692 (Δ20, 22), 1075, 1039 (glycosyl C-0). ¹H-NMR ($C_5D_5N$) δ: 0.66 (3H, S, 18-CH₃), 0.96 (3H, S, 19-CH₃), 1.01 (3H, d, J=6.8 Hz, 27-CH₃), 1.60 (3H, S, 21-CH₃), 4.82 (1H, d, J=7.8 Hz, Glc 1-H),4.92 (1H, d, J=7.8 Hz, Gal 1-H), 5.27 (1H, d, J=7.8 Hz, Glc 1-H), 2.46 (1H, d, J=10.3 Hz, 17-H). ¹³C-NMR data are shown in Table 1. The structure of Compound I was elucidated as (25S)-26-O-β-D-glucopyranosyl-5β-furost-20(22)-ene-3β,26-diol-3-O-β-D-glucopyranosyl(1→2)-β-D-galactopyranoside (anemarsaponin B).

Compound II White amorphous powder, mp>212° C. (dec). It is positive to Liebermann-Burchard, Molish reaction, and Ehrlich's reagent. Anal. calc for $C_{45}H_{74}O_{18}$·2.5H₂O: C 57.02, H 8.34; Found (%): C 56.90, H 8.03. IR $\gamma_{max}$ cm⁻¹: 3354 (OH), 2929, 2850, 1691 (Δ20, 22), 1075, 1037 (glycosyl C—O). FAB-MS m/z 925 (M+Na)⁺, 903 (M+H)⁺, 741 (M+H-Glc)⁺, 579 (M+H-Glc× 2)⁺, 417 (M+H-Glc×3)⁺, 399 (aglycone+H–H₂O)⁺, 255, 185, 145. EI-MS m/z 416 (aglycone)⁺, 398 (aglycone–H₂O)⁺, 344, 343, 325, 287, 273, 255, 217, 201, 181 (base), 163, 139, 109, 95. ¹H-NMR ($C_5D_5N+D_2O$) δ: 0.71 (3H, S, 18-CH₃), 1.01 (3H, S, 19-CH₃), 1.08 (3H, d, J=6.8 Hz, 27-CH₃), 1.68 (3H, S, 21-CH₃), 2.54 (1H, d, J=10.3 Hz, 17-H), 4.86 (1H, d, J=7.8 Hz, Glc 1-H), 4.99 (1H, d, J=7.3 Hz, Glc 1-H), 5.49 (1H, d, J=7.3 Hz, Glc 1-H). ¹³C-NMR data are shown in table 1. The structure of Compound II was elucidated as (25S)-26-O-β-D-glucopyranosyl-5β-furost-20

(22)-ene-3β,26-diol-3-O-β-D-glucopyranosyl(1→2)-β-D-glucopyranoside (anemarsaponin C).

Compound III White amorphous powder, mp>243° C. (dec). It is positive to Liebermann-Burchard, Molish reaction, and Ehrlich's reagent IR $\gamma_{max}$ cm$^{-1}$: 3348 (OH), 2930, 2850, 1075, 1044 (glycosyl C—O). FAB-MS m/z 943 (M+Na)$^+$, 903 (M+H-H$_2$O)$^+$, 741 (M+H-H$_2$O-Glc)$^+$, 579 (M+H-H$_2$O-Glc×2)$^+$, 417 (M+H-H$_2$O-Glc×2-Gal)$^+$, 399 (aglycone+H-H$_2$O×2)$^+$, 255, 185, 145. EI-MS m/z 740 (M-H$_2$O-Glc)$^+$, 578 (M-H$_2$O-Glc×2)$^+$, 416 (aglycone-H$_2$O)$^+$, 415 (aglycone-H-H$_2$O)$^+$, 357, 273, 217, 181, 139. $^1$H-NMR (C$_5$D$_5$N) δ: 0.85 (3H, S, 18-CH$_3$) 0.96 (3H, S, 19-CH$_3$), 1.00 (3H, d, J=6.4 Hz, 27-CH$_3$), 1.30 (3H, d, J=6.8 Hz, 21-CH$_3$), 4.79 (1H, d, J=7.8 Hz, Glc 1-H), 4.90 (1H, d, J=7.8 Hz, Gal 1-H), 5.27 (1H, d, J=7.8 Hz, Glc 1-H). $^{13}$C-NMR data are shown in table 1. The structure of Compound III was elucidated as (25S)-26-β-D-glucopyranosyl-22-hydroxy-5β-furost-3β,26-diol-3-0-β-D-glucopyranosyl(1→2)-β-D-galactopyranoside (prototimosaponin AIII).

Compound IV White amorphous powder, mp 244° C. It is positive to Liebermann-Burchard, Molish reaction, and Ehrlich's reagent. FAB-MS m/z 957 (M+Na)$^+$, 933 (M-H)$^+$, 903 (M+H-MeOH)$^+$, 741 (M+H-MeOH-Glc)$^+$, 579 (M+H-MeOH-Glc×2)$^+$, 417 (M+H-MeOH-Glc×2-Gal)$^+$, 399 (aglycone+H-MeOH-H$_2$O)$^+$. $^1$H-NMR (C$_5$D$_5$N) δ: 0.78 (3H, S, 18-CH$_3$), 0.95 (3H, S, 19-CH$_3$), 1.03 (3H, d, J=6.0 Hz, 27-CH$_3$), 1.16 (3H, d, J=6.6 Hz, 21-CH$_3$), 3.25 (3H, s, 22-OCH$_3$), 4.82 (1H, d, J=7.7 Hz, Glc 1-H), 4.90 (1H, d, J=7.1 Hz, Gal 1-H), 5.27 (1H, d, J=7.7 Hz Glc 1-H). $^{13}$C-NMR data are shown in table 1. The structure of Compound IV was elucidated as (25S)-26-0-β-D-glucopyranosyl-22-methoxy-5β-furost-3β,26-diol-3-0-β-D-glucopyranosyl(1→2)-β-D-galactopyranoside (anemarsaponin E).

Substance V White amorphous powder, mp 271° C. (dec). It is positive to Liebermann-Burchard and Molish reaction, and negtive to Ehrlich reagent. IR $v_{max}$ cm$^{-1}$: 3394, 2930, 1070, 988, 919, 896, 847. FAB-MS (positive) m/z 1057 (M+Na)$^+$, 1035 (M+H)$^+$, 925 (M-Xyl+Na)$^+$, 901 (M-Xyl-H)$^+$, 873 (M-Glc+H)$^+$, 741 (M-Glc-Xyl+H)$^+$, 579 (M-Xyl-Glc×2+H)$^+$, 417 (aglycone+H)$^+$, 399 (aglycone-H$_2$O+H)$^+$. EI-MS m/z 416 (aglycone)$^+$, 398 (aglycone-H$_2$O)$^+$, 357, 347, 344, 302, 287, 273, 181, 139.

Va: $^1$H-NMR (C$_5$D$_5$N) δ: 0.80 (s, C-18 CH$_3$), 0.60 (s, C-19 CH$_3$), 1.12 (d, J=6.7 Hz, C-21 CH$_3$), 0.67 (d, J=5.5 HZ, C-27 CH$_3$), 4.86 (d, J=7.3 Hz, Gal 1-H), 5.17 (d, J=7.9 Hz, Glc(inner) 1-H), 5.21 (d, J=7.9 Hz Xyl 1-H), 5.55 (d, J=7.3 Hz, Glc (terminal) 1-H). $^{13}$C-NMR data are shown in table 2. Compound Va is tigogenin-3-0-β-D-glucopyranosyl(1→2)[β-D-xylopyranosyl(1→3)]-β-D-glucopyranosyl(1→4-β-D-galactopyranoside (degalactotigonin).

Vb: $^1$H-NMR (C$_5$D$_5$N) δ: 0.79 (s, C-18 CH$_3$), 0.60 (s, C-19 CH$_3$), 1.12 (d, J=6.7 Hz, C-21 CH$_3$), 1.05 (d, J=7.3 Hz, C-27 CH$_3$), 4.86 (d, J=7.3 Hz, Gal 1-H), 5.17 (d, J=7.9 Hz, Glc(inner) 1-H) 5.21 (d, J=7.9 Hz Xyl 1-H), 5.55 (d, J=7.3 Hz, Glc(terminal) 1-H). $^{13}$C-NMR data are shown in table 2. Compound Vb is neotigogenin-3-0-β-D-glucopyranosyl(1→2)[β-D-xylopyranosyl(1→3)]-β-D-glucopyranosyl(1→4)-β-D-galactopyranoside (diuranthoside A).

Substance VI White amorphous powder, mp 247° C. (dec). It is positive to Liebermann-Burchard and Molish reaction, and negative to Ehrlich reagent. IR $v_{max}$ cm$^{-1}$: 3408, 2931, 2875, 1072, 987, 922, 897, 847. FAB-MS (positive) m/z 1073 (M+Na)$^+$, 1051 (M+H)$^+$, 595 (M-Xyl-Glc×2+H)$^+$, 433 (aglycone+H)$^+$, 415 (aglycone-H$_2$O+H)$^+$. EI-MS m/z 432 (aglycone)$^+$, 415 (aglycone-H$_2$O+H)$^+$, 414 (aglycone-H$_2$O)$^+$, 373, 363, 360, 342, 318, 303, 300, 289, 271, 139, 126, 115.

VIa: $^1$H-NMR (C$_5$D$_5$N) δ: 0.78 (s, C-18 CH$_3$), 0.67 (s, C-19 CH$_3$) 1.10 (d, J=6.6 Hz, C-21 CH$_3$), 0.67 (C-27 CH$_3$), 4.90 (d, J=7.7 Hz, Gal 1-H), 5.20 (d, J=7.7 Hz, Glc(inner) 1-H), 5.23 (d, J=7.71 Xyl 1-H) 5.57 (d, J=7.7 Hz, Glc (terminal) 1-H). $^{13}$C-NMR data are shown in table 2. Compound VIa is gitogenin-3-O-β-D-glucopyranosyl(1→2)[β-D-xylopyranosyl(1→3)]-β-D-glucopyranosyl(1→4)-β-D-galactopyranoside (F-gitonin).

VIb: $^1$H-NMR (C$_5$D$_5$N) δ: 0.77 (s, C-18 CH$_3$), 0.67 (s, C-19 CH$_3$), 1.10 (d, J=6.6 Hz, C-21 CH$_3$), 1.05 (d, J=7.1 Hz, C-27 CH$_3$), 4.90 (d, J=7.7 Hz, Gal 1-H), 5.20 (d, J=7.7 Hz, Glc(inner) 1-H), 5.23 (d, J=7.7 Hz Xyl 1-H), 5.57 (d, J=7.7 Hz, Glc(terminal) 1-H). $^{13}$C-NMR data are shown in table 2. Compound VIb is neogitogenin-3-0-β-D-glucopyranosyl(1→2)[β-D-xylopyranosyl(1→3)]-β-D-glucopyranosyl(1→4)-β-D-galactopyranoside (anemarsaponin F).

Substance VII White amorphous powder, mp 242° C. It is positive to Liebermann-Burchard and Molish reaction, and negtive to Ehrlich reagent IR $v_{max}$ cm$^{-1}$: 3394, 2934, 1069, 985, 919, 896, 847. FAB-MS (positive) m/z 1055 (M+Na)$^+$, 1033 (M+R)$^+$, 737 (M-Glc-Xyl-H)$^+$, 577 (M-Xyl-Glc×2+H)$^+$, 415 (aglycone+H)$^+$, 397 (aglycone-H$_2$O+H)$^+$. EI-MS m/z 414 (aglycone)$^+$, 396 (aglycone-H$_2$O)$^+$, 355, 345, 342, 300, 282, 271, 139.

VIIa: $^1$H-NMR (C$_5$D$_5$N) δ: 0.79 (s, C-18 CH$_3$), 0.85 (s, C-19 CH$_3$) 1.13 (d, J=6.7 Hz, C-21 CH$_3$), 0.67 (d, J=5.5 HZ, C-27 CH$_3$), 4.87 (d, J=7.4 Hz, Gal 1-H), 5.16 (d, J=7.9 Hz, Glc(inner) 1-H), 5.22 (d, Xyl 1-H), 5.55 (d, J=7.9 Hz, Glc (terminal) 1-H). $^{13}$C-NMR data are shown in table 2. Compound VIIa is diosgenin-3-0-β-D-glucopyranosyl(1→2)[β-D-xylopyranosyl(1→3)]-β-D-glucopyranlsyl(1→4)-β-D-galactopyranoside (aspidistrin).

VIIb: $^1$H-NMR (C$_5$D$_5$N) δ: 0.79 (s, C-18 CH$_3$), 0.85 (s, C-19 CH$_3$), 1.13 (d, J=6.7 Hz, C-21 CH$_3$), 1.05 (d, J=6.7 Hz, C-27 CH$_3$), 4.87 (d, J=7.4 Hz, Gal 1-H), 5.16 (d, J=7.9 Hz, Glc(inner) 1-H) 5.22 (d, Xyl 1-H), 5.55 (d, J=7.9 Hz, Glc(terminal) 1-H). $^{13}$C-NMR data are shown in table 2. Compound VIIb is yamogenin-3-0-β-D-glucopyranosyl(1→2)[β-D-xylopyranosyl(1→3)]-β-D-glucopyranosyl(1→4)-β-D-galactopyranoside(3-O-β-lycotetrasoyl yamogenin).

Substance VIII White amorphous powder, mp 258° C. (dec). It is positive to Liebermann-Burchard and Molish reaction, and negative to Ehrlich reagent. IR $v_{max}$ cm$^{-1}$: 3414, 2940, 2902, 1071, 988, 920, 895, 849. FAB-MS (positive) m/z 1071 (M+Na)$^+$, 1049 (M+H)$^+$, 855 (M-Glc-H)$^+$, 753 (M-Glc-Xyl-H)$^+$, 593 (M-Xyl-Glc×2+H)$^+$, 431 (aglycone+H)$^+$, 413 (aglycone-H$_2$O+H)$^+$, 395 (aglycone-H$_2$O×2+H)$^+$. EI-MS m/z 430 (aglycone)$^+$, 413 (aglycone-H$_2$O+H)$^+$, 412 (aglycone-H$_2$O)$^+$, 371, 361, 358, 316, 298, 287, 269, 139, 126, 115.

VIIIa: $^1$H-NMR (C$_5$D$_5$N) δ: 0.78 (s, C-18 CH$_3$), 0.91 (s, C-19 CH$_3$), 1.11 (d, J=6.6 Hz, C-21 CH$_3$), 0.67 (d, J=5.5 Hz, C-27 CH$_3$), 4.91 (d, J=7.7 Hz, Gal 1-H), 5.20 (d, J=7.7 Hz, Glc(inner) 1-H), 5.23 (d, J=7.7 Hz Xyl 1-H), 5.57 (d, J=7.7 Hz, Glc(terminal) 1-H). $^{13}$C-NMR data are shown in table 2. Compound VIIIa is yuccagenin-3-0-β-D-glucopyranosyl(1→2)[β-D-glucopyranosyl(1→3)]-β-D-glucopyranosyl(1→4)-β-D-galactopyranoside (karatavioside A).

VIIIb: $^1$H-NMR (C$_5$D$_5$N) δ: 0.78 (s, C-18 CH$_3$), 0.91 (s, C-19 CH$_3$), 1.11 (d, J=6.6 Hz, C-21 CH$_3$), 1.05 (d, J=7.1 Hz, C-27 CH$_3$), 4.91 (d, J=7.7 Hz, Gal 1-H), 5.20 (d, J=7.7 Hz, Glc(inner) 1-H), 5.23 (d, J=7.7 Hz Xyl 1-H), 5.57 (d, J=7.7

Hz, Glc(terminal) 1-H). $^{13}$C-NMR data are shown in table 2. Compound VIIIb is lilagenin-3-0-β-D-glucopyranosyl(1→2)[β-D-xylopyranosyl(1→3)]-β-D-glucopyranosyl(1→4)-β-D-galactopyranoside (anemarsaponin G).

TAB 1

$^{13}$C—NMR chemical shifts of compound I–IV in C$_5$D$_5$N

| carbon | I | II | III | IV |
|---|---|---|---|---|
| Aglycone | | | | |
| 1 | 30.9 | 30.7 | 30.9 | 30.9 |
| 2 | 26.9 | 26.9 | 27.0 | 27.0 |
| 3 | 75.1 | 75.2 | 75.0 | 75.2 |
| 4 | 30.9 | 30.9 | 30.9 | 31.0 |
| 5 | 36.9 | 36.8 | 36.9 | 36.9 |
| 6 | 26.8 | 26.8 | 26.7 | 26.7 |
| 7 | 26.8 | 26.8 | 26.7 | 26.7 |
| 8 | 35.1 | 35.1 | 35.4 | 35.5 |
| 9 | 40.1 | 40.1 | 40.2 | 40.2 |
| 10 | 35.2 | 35.1 | 35.2 | 35.2 |
| 11 | 21.2 | 21.3 | 21.1 | 21.0 |
| 12 | 40.0 | 40.0 | 40.4 | 40.5 |
| 13 | 43.8 | 43.8 | 41.2 | 41.2 |
| 14 | 54.7 | 54.7 | 56.4 | 56.4 |
| 15 | 31.3 | 31.3 | 32.4 | 32.1 |
| 16 | 84.5 | 84.5 | 81.2 | 81.4 |
| 17 | 64.6 | 64.6 | 64.0 | 64.4 |
| 18 | 14.6 | 14.3 | 16.7 | 16.5 |
| 19 | 24.0 | 24.0 | 24.0 | 24.0 |
| 20 | 103.5 | 103.5 | 40.6 | 41.2 |
| 21 | 11.8 | 11.8 | 16.4 | 16.4 |
| 22 | 152.3 | 152.3 | 110.6 | 112.6 |
| 23 | 34.4 | 34.3 | 37.1 | 30.9 |
| 24 | 23.6 | 23.6 | 28.3 | 28.2 |
| 25 | 33.7 | 33.6 | 34.4 | 34.4 |
| 26 | 75.2 | 75.2 | 75.3 | 75.2 |
| 27 | 17.1 | 17.1 | 17.4 | 17.5 |
| OCH3 | | | | 47.3 |
| Galactose or glucose (inner C-3) | | | | |
| 1 | 102.6 | 101.9 | 102.5 | 102.5 |
| 2 | 81.8 | 83.1 | 81.8 | 81.7 |
| 3 | 76.9 | 78.5 | 76.9 | 76.9 |
| 4 | 69.8 | 71.7 | 69.8 | 69.8 |
| 5 | 76.6 | 78.2 | 76.5 | 76.6 |
| 6 | 62.1 | 62.8 | 62.1 | 62.1 |
| glucose (terminal C-3) | | | | |
| 1 | 106.1 | 105.9 | 106.1 | 106.0 |
| 2 | 75.5 | 77.0 | 75.5 | 75.4 |
| 3 | 78.0 | 77.9 | 78.0 | 78.0 |
| 4 | 71.6 | 71.5 | 71.6 | 71.7 |
| 5 | 78.4 | 78.5 | 78.4 | 78.5 |
| 6 | 62.7 | 62.6 | 62.7 | 62.8 |
| C-26 glucose | | | | |
| 1 | 105.1 | 105.1 | 105.1 | 105.0 |
| 2 | 75.2 | 75.2 | 75.2 | 75.0 |
| 3 | 78.5 | 78.5 | 78.5 | 78.6 |
| 4 | 71.6 | 71.6 | 71.6 | 71.7 |
| 5 | 78.5 | 78.2 | 78.4 | 78.4 |
| 6 | 62.7 | 62.8 | 62.7 | 62.8 |

TABLE 2

$^{13}$C—NMR chemical shifts of Compounds Va–VIIIb (100 MHz, in C$_5$D$_5$N)

| | Va | Vb | VIa | VIb | VIIa | VIIb | VIIIa | VIIIb |
|---|---|---|---|---|---|---|---|---|
| Aglycone | | | | | | | | |
| 1 | 37.1 | | 45.5 | | 37.5 | | 45.7 | |
| 2 | 29.8 | | 70.7 | | 30.1 | | 70.7 | |
| 3 | 77.4 | | 84.2 | | 78.3 | | 84.4 | |
| 4 | 34.8 | | 34.0 | | 39.2 | | 37.6 | |
| 5 | 44.6 | | 44.5 | | 141.0 | | 140.0 | |
| 6 | 28.8 | | 28.0 | | 121.6 | | 121.9 | |
| 7 | 32.3 | | 32.1 | | 32.3 | | 32.1 | |
| 8 | 35.2 | | 34.5 | | 31.8 | | 31.0 | |
| 9 | 54.3 | | 54.3 | | 50.3 | | 50.1 | |
| 10 | 35.7 | | 36.8 | | 37.0 | | 37.9 | |
| 11 | 21.2 | | 21.4 | | 21.1 | | 21.1 | |
| 12 | 40.1 | | 40.0 | | 39.9 | | 39. | |
| 13 | 40.7 | | 40.7 | | 40.4 | | 40.4 | |
| 14 | 56.4 | | 56.2 | | 56.6 | | 56.4 | |
| 15 | 32.1 | | 32.1 | | 32.1 | | 32.1 | |
| 16 | 81.1 | 81.2 | 81.2 | | 81.1 | 81.2 | 81.1 | |
| 17 | 62.9 | 62.8 | 62.9 | | 62.9 | 62.7 | 62.6 | |
| 18 | 16.5 | 16.3 | 16.6 | | 16.4 | 16.3 | 16.3 | |
| 19 | 12.2 | | 13.4 | | 19.4 | | 20.4 | |
| 20 | 41.9 | 42.4 | 41.9 | 42.4 | 42.0 | 42.5 | 41.9 | 42.4 |
| 21 | 15.0 | 14.8 | 15.0 | 14.8 | 15.0 | 14.9 | 15.0 | 14.9 |
| 22 | 109.2 | 109.7 | 109.2 | 109.7 | 109.3 | 109.8 | 109.2 | 109.7 |
| 23 | 31.8 | 26.3 | 31.7 | 26.3 | 31.6 | 26.4 | 31.7 | 26.3 |
| 24 | 29.2 | 26.1 | 29.2 | 26.2 | 29.3 | 26.2 | 29.2 | 26.1 |
| 25 | 30.5 | 27.5 | 30.5 | 27.5 | 30.6 | 27.5 | 30.5 | 27.5 |
| 26 | 66.8 | 65.0 | 66.8 | 65.0 | 66.9 | 65.1 | 66.8 | 65.0 |
| 27 | 17.3 | 16.2 | 17.3 | 16.2 | 17.3 | 16.3 | 17.3 | 16.3 |
| Galactose | | | | | | | | |
| 1 | 102.4 | | 103.2 | | 102.7 | | 103.3 | |
| 2 | 73.1 | | 72.5 | | 73.1 | | 72.6 | |
| 3 | 75.0 | | 75.1 | | 75.1 | | 75.1 | |
| 4 | 79.8 | | 79.3 | | 79.8 | | 79.2 | |
| 5 | 75.3 | | 75.7 | | 75.3 | | 75.6 | |
| 6 | 60.6 | | 60.6 | | 60.6 | | 60.6 | |
| Glucose(inner) | | | | | | | | |
| 1 | 104.7 | | 104.6 | | 104.8 | | 104.6 | |
| 2 | 81.2 | | 81.1 | | 81.3 | | 81.1 | |
| 3 | 86.7 | | 86.9 | | 86.8 | | 86.9 | |
| 4 | 70.4 | | 70.4 | | 70.4 | | 70.0 | |
| 5 | 78.5 | | 78.1 | | 78.6 | | 78.1 | |
| 6 | 62.4 | | 62.6 | | 63.3 | | 62.8 | |
| Glucose(terminal) | | | | | | | | |
| 1 | 104.8 | | 104.7 | | 104.9 | | 104.7 | |
| 2 | 75.5 | | 75.4 | | 75.5 | | 75.4 | |
| 3 | 78.5 | | 78.4 | | 78.8 | | 78.4 | |
| 4 | 70.7 | | 71.3 | | 70.8 | | 71.3 | |
| 5 | 77.5 | | 78.7 | | 77.6 | | 78.7 | |
| 6 | 63.0 | | 62.9 | | 62.9 | | 62.9 | |
| Xylose | | | | | | | | |
| 1 | 105.0 | | 104.9 | | 105.1 | | 104.9 | |
| 2 | 76.1 | | 76.0 | | 76.2 | | 76.0 | |
| 3 | 77.7 | | 77.5 | | 77.1 | | 77.5 | |
| 4 | 71.0 | | 70.4 | | 71.0 | | 70.3 | |
| 5 | 67.2 | | 67.3 | | 67.3 | | 67.3 | |

According to the methods of examples 1 and 2, the following compounds are obtained from the plants.

1*(25S)-26-0-β-D-glucopyranosyl-22-hydroxy-5β-furost-2β,3β,26-triol-
3-O-β-D-glucopyranosyl(1→2)-β-D-galactopyranoside;
2*(25S)-26-0-β-D-glucopyranosyl-22-methoxy-5β-furost-2β,3β,26-triol-
3-O-β-D-glucopyranosyl(1→2)-β-D-galactopyranoside;
3*(25S)-26-0-β-D-glucopyranosyl-5β-furost-20(22)-ene-2β,3β,26-triol-
3-O-β-D-glucopyranosyl(1→2)-β-D-galactopyranoside.

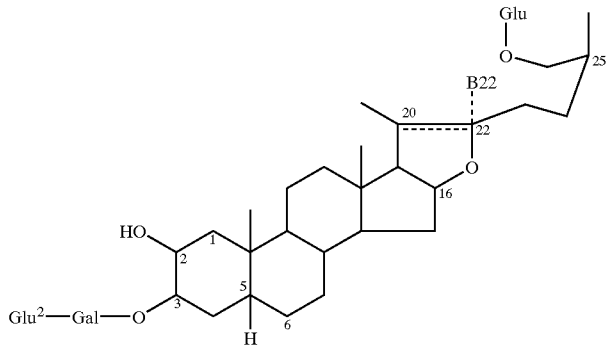

Compound 1*: R22 = OH, $C_{20}$–$C_{22}$ is a single bond
Compound 2*: R22 = $OCH_3$, $C_{20}$–$C_{22}$ is a single bond
Compound 3*: R22 is absent, $C_{20}$–$C_{22}$ is a double bond $^{13}$C-NMR data:

| Carbon | 1* | 2* | 3* |  |  | 1* | 2* | 3* |
|---|---|---|---|---|---|---|---|---|
| 1 | 40.6 | 40.6 | 40.6 | Gal | 1 | 106.1 | 106.1 | 106.1 |
| 2 | 67.2 | 67.2 | 67.2 |  | 2 | 75.2 | 75.1 | 75.2 |
| 3 | 81.8 | 81.8 | 81.8 |  | 3 | 78.1 | 78.1 | 78.1 |
| 4 | 31.9 | 31.9 | 31.9 |  | 4 | 71.9 | 71.9 | 71.8 |
| 5 | 36.6 | 36.6 | 36.6 |  | 5 | 78.4 | 78.5 | 78.4 |
| 6 | 26.6 | 26.6 | 26.6 |  | 6 | 62.9 | 62.9 | 62.9 |
| 7 | 26.3 | 26.3 | 26.3 | Glu | 1 | 103.3 | 103.3 | 103.3 |
| 8 | 35.6 | 35.6 | 35.6 |  | 2 | 81.7 | 81.6 | 81.7 |
| 9 | 41.5 | 41.5 | 41.5 |  | 3 | 77.0 | 77.0 | 77.0 |
| 10 | 37.1 | 37.1 | 37.1 |  | 4 | 69.8 | 69.9 | 69.9 |
| 11 | 21.4 | 21.4 | 21.5 |  | 5 | 76.9 | 76.9 | 76.9 |
| 12 | 40.4 | 40.4 | 40.0 |  | 6 | 62.0 | 62.1 | 62.0 |
| 13 | 41.3 | 41.3 | 43.9 | Glu | 1 | 105.1 | 105.0 | 105.0 |
| 14 | 56.3 | 56.3 | 54.6 | (C-26) | 2 | 75.2 | 75.1 | 75.2 |
| 15 | 32.4 | 32.1 | 31.3 |  | 3 | 78.6 | 78.6 | 78.6 |
| 16 | 81.2 | 81.4 | 84.5 |  | 4 | 71.8 | 71.7 | 71.8 |
| 17 | 64.0 | 64.4 | 64.6 |  | 5 | 78.4 | 78.4 | 78.4 |
| 18 | 16.7 | 16.5 | 14.5 |  | 6 | 62.9 | 62.8 | 62.9 |
| 19 | 23.9 | 24.0 | 23.9 |  |  |  |  |  |
| 20 | 40.7 | 41.2 | 103.5 |  |  |  |  |  |
| 21 | 16.4 | 16.4 | 11.8 |  |  |  |  |  |
| 22 | 110.7 | 112.6 | 152.3 |  |  |  |  |  |
| 23 | 37.1 | 30.9 | 34.4 |  |  |  |  |  |
| 24 | 28.3 | 28.2 | 23.6 |  |  |  |  |  |
| 25 | 34.4 | 34.4 | 33.6 |  |  |  |  |  |
| 26 | 75.4 | 75.2 | 75.2 |  |  |  |  |  |
| 27 | 17.5 | 17.5 | 17.1 |  |  |  |  |  |
| $OCH_3$ |  | 47.3 |  |  |  |  |  |  |

FAB-MS:
1*FAB-MS m/z: 919(M+H—$H_2O$)$^+$, 757(M+H—$H_2O$—Glu)$^+$, 595(M+H—$H_2O$—Glu × 2), 433(M+H—$H_2O$—Glu × 2-Gal)$^+$, 415(aglycone+H—$H_2O$ × 2)$^+$, 271, 255, 145
2*FAB-MS m/z: 951(M+H)$^+$, 919(M+H—MeOH)$^+$, 757(M+H—MeOH—Glu)$^+$, 595(M+H—MeOH—Glu × 2)$^+$, 433(M+H—MeOH—Glu × 2-Gal)$^+$, 415(aglycone+H—MeOH—$H_2O$)
3*FAB-MS m/z: 919(M+H)$^+$, 757(M+H—Glu)$^+$, 595(M+H—Glu × 2)$^+$, 433(M+H—Glu × 2-Gal)$^+$, 415(aglycone+H—$H_2O$)$^+$ 1**(25R)-26-0-β-D-glucopyranosyl-22-hydroxy-5-ene-furost-3β,26-diol-3-O-β-D-glucopyranosyl(1→4)-β-D-galactopyranoside;
2**(25R)-26-0-β-D-glucopyranosyl-22-methoxy-5-ene-furost-3β,26-diol-3-O-β-D-glucopyranosyl(1→4)-β-D-galactopyranoside;
3**(25R)-26-0-β-D-glucopyranosyl-5-ene-furost-20(22)-ene-3β,26-diol-3-O-β-D-glucopyranosyl(1→4)-β-D-galactopyranoside;

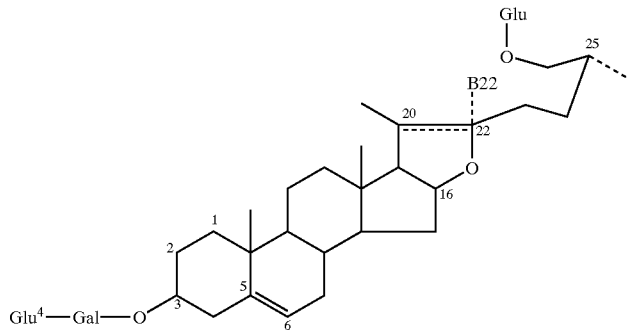

Compound 1**: R22 = OH, $C_{20}$–$C_{22}$ is a single bond
Compound 2**: R22 = $OCH_3$, $C_{20}$–$C_{22}$ is a single bond
Compound 3**: R22 is absent, $C_{20}$–$C_{22}$ is a double bond $^{13}$C-NMR data:

| Carbon | 1 | 2 | 3 |  |  | 1 | 2 | 3 |
|---|---|---|---|---|---|---|---|---|
| 1 | 37.6 | 37.6 | 37.6 | Gal | 1 | 103.0 | 103.0 | 103.0 |
| 2 | 30.4 | 30.4 | 30.4 |  | 2 | 73.5 | 73.5 | 73.4 |
| 3 | 78.4 | 78.4 | 78.4 |  | 3 | 75.4 | 75.4 | 75.3 |
| 4 | 39.4 | 39.4 | 39.4 |  | 4 | 79.8 | 79.8 | 79.8 |
| 5 | 141.2 | 141.2 | 141.2 |  | 5 | 75.9 | 75.8 | 75.9 |
| 6 | 121.6 | 121.6 | 121.6 |  | 6 | 61.0 | 61.0 | 61.0 |
| 7 | 32.4 | 32.4 | 32.4 | Glu | 1 | 107.0 | 107.1 | 107.0 |
| 8 | 31.9 | 31.9 | 31.9 |  | 2 | 75.2 | 75.2 | 75.2 |
| 9 | 50.5 | 50.5 | 50.5 |  | 3 | 78.4 | 78.4 | 78.2 |
| 10 | 37.2 | 37.2 | 37.2 |  | 4 | 72.4 | 72.6 | 72.4 |
| 11 | 21.3 | 21.3 | 21.4 |  | 5 | 78.7 | 78.7 | 78.6 |
| 12 | 40.1 | 40.1 | 40.0 |  | 6 | 63.1 | 63.1 | 63.2 |
| 13 | 40.6 | 40.6 | 43.2 | Glu | 1 | 104.6 | 104.9 | 104.7 |
| 14 | 56.8 | 56.8 | 55.1 | (C-26) | 2 | 75.0 | 75.1 | 75.1 |
| 15 | 32.4 | 32.4 | 31.3 |  | 3 | 78.3 | 78.6 | 78.3 |
| 16 | 80.9 | 81.2 | 84.2 |  | 4 | 71.6 | 71.9 | 71.6 |
| 17 | 63.6 | 64.2 | 64.2 |  | 5 | 78.0 | 78.2 | 77.9 |
| 18 | 16.5 | 16.3 | 14.3 |  | 6 | 62.8 | 63.1 | 62.9 |
| 19 | 19.4 | 19.5 | 19.4 |  |  |  |  |  |
| 20 | 40.6 | 40.6 | 103.2 |  |  |  |  |  |
| 21 | 16.2 | 16.2 | 11.6 |  |  |  |  |  |
| 22 | 110.9 | 112.8 | 152.1 |  |  |  |  |  |
| 23 | 37.0 | 30.9 | 34.3 |  |  |  |  |  |
| 24 | 28.3 | 28.3 | 23.5 |  |  |  |  |  |
| 25 | 34.2 | 34.3 | 33.4 |  |  |  |  |  |
| 26 | 75.3 | 75.3 | 75.2 |  |  |  |  |  |
| 27 | 17.4 | 17.2 | 17.1 |  |  |  |  |  |
| OCH3 |  | 47.4 |  |  |  |  |  |  |

Pharmacological Experiments

Dementia is a group of progressive mental deterioration diseases defined by global cognitive decline involving gradual loss of memory, reasoning, judgment, and orientation. It mainly includes Alzheimer's disease (AD), vascular dementia (VD), mixed dementia and some other types. Their etiological factors are complicated and the mechanism of AD is still unclear even now. The inventors observed the anti-dementia activities of steroidal saponins from *Anemarrhena asphodeloides Bge.*, especially compound III (prototimosaponin AIII), at different angles.

The Influence on the Cerebral Circulation and Metabolism

Development of drugs for treating dementia is to be considered the pathogenesis of dementia. For the vascular dementia, we want to know whether the steroidal saponins from *Anemarrhena asphodeloides Bge.* can dilate the blood vessel, especially cerebralvascular, and whether they can improve the cerebral blood flow in vivo model.

1. Experiment on Cerebral Basilar Artery:
   Methods:
   (1). 1 mg of compound I, II, III, IV dissolved in 1 ml saline respectively. Take 50 μl solutions to dissolved in 5 ml saline again.
   (2). Remove the cerebrum and cerebellum from the fresh brain, and get the middle part of the basilar artery
   (3). Adjust the transducer and amplifier to make pointer return to zero
   (4). Hang the basilar artery on the transducer and immerse it in the bath.
   Results:
   (1). The basilar artery dilated slightly after 50 μl compound III was added to the bath, and did not contract again when adding the vasoconstrictor KCl.
   (2). There is no obvious effect when the same volume solution of compound I, II, or IV was added
   (3). Repeated this experiment and got the same results.
   The result showed that compound III could dilate cerebral vascular and resist the contraction caused by vasoconstrictor at the concentration of $10^{-5}$ g/ml (0.01 mM), which is two orders of magnitude lower than that of positive Ligustrazine at the same experimental conditions.

2. Experiment on Rat Thoracic Aorta
   Methods:
   Take thoracic aorta from rat, remove the connective tissue and blood, immerse the aorta into the Krebs-Henselelt liquid and ventilate oxygen, hang the aorta on the transducer, and assay its radial tension.
   Results. FIG. 1.
   FIG. 1 showed that compound III could restrain the contraction of rat aorta caused by KCl at a concentration of 0.04 mM.

3. The Effect on Cerebral Blood Flow of Rat:
   After in vitro experiments, we observed the influence of compound III on the cerebral blood flow in vivo model.
   Method: Hydrogen-clearing method
   Instrument: LS-III Blood Flow Meter
   Animal: Wister rat, male
   Methods and Procedures:
   1. Anesthetize the rat with 10% chloral hydrate, separate the general vein of thigh and intubate to prepare to inject Compound III.
   2. Open a window in the parietal lobe of dermal epithelium with cranial drill and lay up hydrogen electrode.
   3. After operation, collect the animal with the Blood Follow Meter and computer, steady for 30 minutes and begin to measure the rCBF (regional cerebral blood flow). Results: The following Table and FIG. 2.

Conclusions and Discussions:
1. It is displayed that compound III can increase the rCBF of rat by 26.5% at the concentration of 50 μg/kg in vivo. This indicates that compound III can improve cerebral blood circulation and metabolism, so it benefits the improvement of dementia, especially vascular dementia.
2. Hemolysis is the biggest problem for saponin. It is observed that there is no hemolysis when administering compound III intravenously at this effective concentration.

The Effect of Compound III on Nicotinic Receptors

Cholinergic system has much to do with cognition. Recently, epidemiological investigation, pathological study and some medicine's activities (such as tacrine) showed that nicotinic receptors play an important role in AD. Since the late 1980s, some experiments almost unanimously displayed that the number of N receptor in cerebra tissue of patients with AD is 50% less than that of normal people. There is lopsided development between the high affinity binding sites of cerebra N receptors and the low, and the proportion of the high decreases comparatively. The number of peripheral N receptors decreases as well. Nicotine can up-regulate the number of nicotinic receptors, and improve memory and attention. But nicotine presents several potential problems (side effects) as an anti-dementia drug. So researchers had tried to develop a series of nicotine derivatives as anti-dementia drugs, which selectively interact with central nicotinic receptors.

In the experiments, we used two different cell lines, SY-SH5Y and M10. SY-SH5Y is human neuroblastoma cell which expresses natural nicotinic and muscarinic receptors, and M10 cell expresses the recombinant a4b2 subtype of chicken nicotinic receptor. We treated both cell lines with Compound III for three days with different concentrations from 1 μM up to 100 μM, and measured the amount of nAChRs. The results are shown in FIG. 3 and FIG. 4.

The treatment can significantly up-regulate the number of nAChRs and this effect was concentration-dependent Compound III showed similar potency as nicotine in up-regulating the number of nAChRs. It is one of the main constituents of *Anemarrhena asphodeloides* Bge which has been used in China for over one thousand years, and it has almost no toxicity. Moreover, its structure is very different from nicotine, so we hope we can find a new kind of anti-dementia compounds which interact with the nicotinic receptors.

| Effect of Compound III (50 μg/Kg) on cerebral blood flood (rCBF) | | | | | | |
|---|---|---|---|---|---|---|
| Time (min) | Rat 1 (ml/mg/min) | Rat 2 (ml/mg/min) | Rat 3 (ml/mg/min) | Rat 4 (ml/mg/min) | Mean of rCBF (ml/mg/min) | Rate of rCBF increase (%) |
| 0 | 114.17 | 130.86 | 144.25 | 135.97 | 131.3125 | 0 |
| 1 | 133.30 | 150.05 | 139.55 | 143.35 | 141.5625 | 7.805810 |
| 10 | 147.99 | 143.41 | 162.10 | 145.64 | 149.7850 | 14.06759 |
| 20 | 158.46 | 136.33 | 177.59 | 121.24 | 148.4050 | 13.01666 |
| 30 | 164.61 | 182.96 | 171.42 | 135.00 | 163.4975 | 24.51023 |
| 40 | 176.90 | 202.46 | 165.94 | 113.38 | 164.6700 | 25.40314 |
| 50 | 176.77 | 193.57 | 163.08 | 131.17 | 166.1475 | 26.52832 |

Effect on the Proliferation of Rat Hippocampus Neuronal Cells

Methods:
1. Get hippocampus neuronal cells from rat embryo and do preliminary cell culture.
2. Incubate the cells for 7 days at different concentration (3 or 5 parallel holes for each group).
3. Do MTT staining and measure OD value.

Results:
Effect on the proliferation of rat hippocampus cells

| Sample Concentration ($\mu$g/ml) | Compound III | | Crude furostanol saponins ZMZ | |
|---|---|---|---|---|
| | Mean of OD | Proliferation rat (%) | Mean of OD | Proliferation rate (%) |
| control | 0.0624 | 0 | 0.0624 | 0 |
| 0.1 | 0.0773 | 23.87821 | — | — |
| 1 | 0.0663 | 6.25000 | 0.0600 | −3.84615 |
| 10 | 0.0860 | 37.82051 | 0.0600 | −3.84615 |
| 50 | 0.0807 | 29.32692 | 0.0480 | −23.07692 |
| 100 | 0.0750 | 20.19231 | 0.0417 | −33.17308 |
| 500 | 0.0903 | 44.71154 | 0.0577 | −7.53205 |
| 1000 | 0.0673 | 7.85256 | — | — |

The preliminary cell culture experiments showed that Compound III could promote the proliferation of the rat hippocampus neuronal cells. On the seventh day of exposure to this compound, the increase in the number of cells in each group ranged from 23.9% to 44.7% at concentrations ranging from 0.1 $\mu$M to 500 $\mu$M.

Scavenging Effects on Hydroxyl Free Radicals

Free radical reaction is now considered to be one of the prominent factors which cause injuries of the structure and function of nerve cell membrane. There has been a growing consensus that free radicals mediated neuronal damage may be a major contributor to the etiology of Alzheimer's disease. Some researchers are developing some free radical scavengers to treat dementia. We studied the scavenging effects of the saponins from *Anemarrhena asphodeloides Bge.* on hydroxyl free radicals by ESR (electron spin resonance) method.

1. Materials and Methods:

Hydroxyl free radical is generated by Fenton reaction: mix 5 $\mu$l 2 mM FeSO4, 10 $\mu$l 0.8 mM DMPO and 5 $\mu$l 50 mM EDTA together, add 5 $\mu$l $H_2O_2$ to the mixture, then add 25 $\mu$l saponin or distilled water, mix and put the solution into quartz capillary, and measure it 1 minute later.

The experiment is completed on ESP 300 ESR Spectrum Meter. Conditions: room temperature, CF=3470 GS, SW=200 GS, MF=25 KHz, MA=1 GS, CT=84 S, P (power)=10 mw.

Weight Compound I, II, III, IV, V, VI, VII, VIII respectively, add distill water to make 10 mg/ml solutions. Add each of the solutions to hydroxyl free radical system at a proportion of 1:1. Distill water acts as the blank control at the same condition. Measure the extent of ESR spectrum signal.

Calculate clearance rate on the basis of following formula:

$$E(\%) = (ho - hx)/ho \times 100$$

"ho" represents altitude of the ESR spectrum peak of control

"hx" represents altitude of the corresponding peak when a saponin is added

2. Results:
Scavenging effects of Compound I–VIII on free radicals

| Sample | Concentration(mg/ml) | Scavenging rate(%) |
|---|---|---|
| Control | 0 | 0.0 |
| I | 5 | 23.3 |
| II | 5 | 40.0 |
| III | 5 | 56.7 |
| IV | 5 | 33.3 |
| V | 5 | 23.3 |
| VI | 5 | 0.0 |
| VII | 5 | −20.0 |
| VIII | 5 | 0.0 |

The results showed that Compound I, II, III, IV could scavenge the hydroxyl free radicals produced by Fenton reaction ($Fe^{2+} + H_2O_2$). The effect of Compound III is the most effective. At the concentration of 5 mM, its inhibitory rate is 56.7%. Substance V, VI, VII and VIII had no scavenging effect, maybe because they are not water soluble. The experiment suggests that Compound III's anti-dementia activity may be related to its scavenging effects on free radicals.

What is claimed is:

1. A method for the prophylaxis or treatment of dementia comprising administering a prophylactically or treatment effective amount of a compound of Formula I or stereoisomer thereof to a subject in need of such prophylaxis or treatment, Formula I

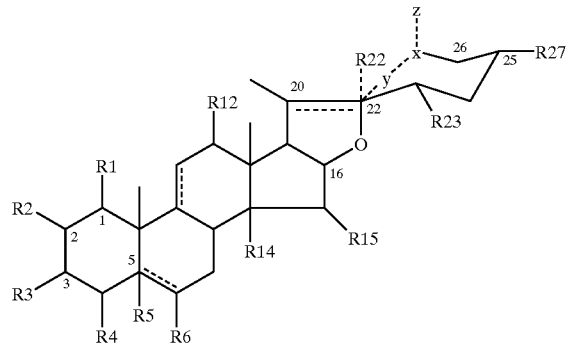

wherein $R_1$ is hydrogen, —OH, —O-Xyl, —O-Ara-Rha, —O-Fuc-Rha, —O-Ara-Rha,

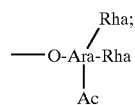

$R_2$ is hydrogen, —OH, —O-Fuc, —O-Rha, or —O-Glu;

$R_3$ is —OCOCH$_3$, —OCOC$_{15}$H$_{31}$, or

—O-Gal-Glu,

—O-Glu-Glu,

—O-Glu-Ara,

—O-Fuc-Glu,

—O-Rha-Glu,

—O-Glu-Glu-Glu,

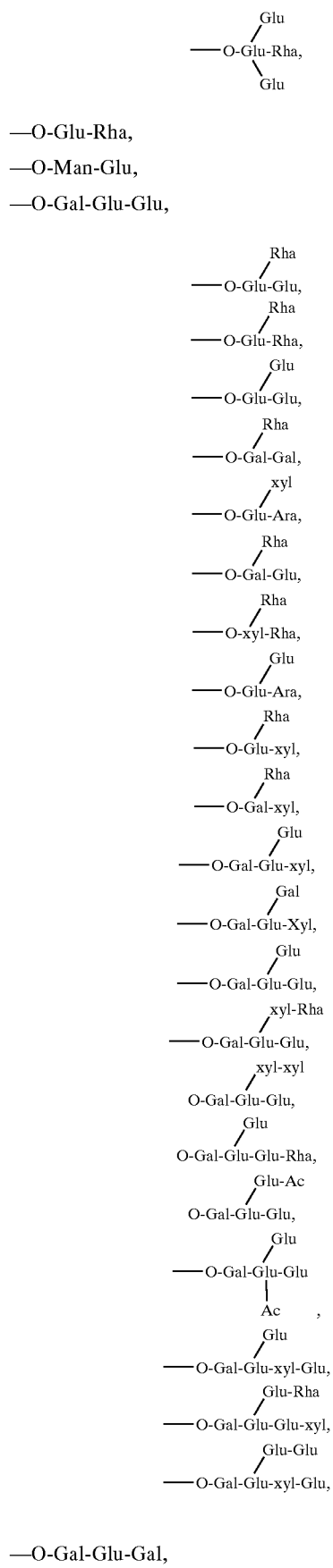

—O-Gal-Glu-Gal,

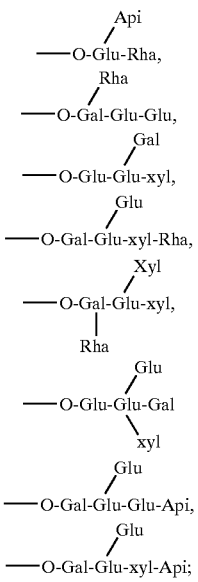

$R_4$ is hydrogen, —OH, or —OSO$_3$Na, $R_5$ is hydrogen, hydroxy, —O-Glu, or is absent, $R_6$ is hydrogen, —OH, oxo(=O), —O-Qui-Rha, or —O-Qui-Xyl;

$R_{12}$ is hydrogen, —OH, or oxo(=O);

$R_{14}$ is hydrogen, or —OH;

$R_{15}$ is hydrogen, or —OH;

$R_{22}$ is hydroxy, or O(CH$_2$)$_n$CH$_3$, n=0~3, or is absent, $R_{23}$ is hydrogen, or —OH;

$R_{27}$ is —CH$_3$, —CH$_2$OH, or =CH$_2$;

X is O, or NH;

=== denotes a single bond or a double bond,

Y is a direct bond or is absent,

Z is Glu or is absent, provided that a compound of Formula I wherein $R_1=R_2=R_4=R_6=R_{12}=R_{14}=R_{15}=R_{23}$=H, $R_3$=β-OH, $R_5$=β-H, X=O, === is a single bond, Y is a direct bond, $R_{22}$ is absent, Z is absent, $R_{27}$ is —CH$_3$, and $C_{25}$ is (S) configuration, is not included.

2. A method of claim 1, wherein $R_1=R_2=R_4=R_6=R_{12}=R_{14}=R_{15}=R_{23}$=H, $R_3$ is —O-β-Gal$^2$-β-Glu, $R_5$=β-H, $R_{27}$=—CH$_3$, $C_{25}$ is S-configuration, X is O, Z is -β-Glu, Y is absent, $R_{22}$ is absent, the dotted line between position $C_{20}$–$C_{22}$ is a double bond, and other === is a single bond.

3. A method of claim 1, wherein $R_1=R_2=R_4=R_6=R_{12}=R_{14}=R_{15}=R_{23}$=H, $R_3$ is —O-β-Glu$^2$-β-Glu, $R_5$=β-H, $R_{27}$=—CH$_3$, $C_{25}$ is S-configuration, X is O, Z is -β-Glu, Y is absent, $R_{22}$ is absent, the dotted line between position $C_{20}$–$C_{22}$ is a double bond, and other === is a single bond.

4. A method of claim 1, wherein $R_1=R_2=R_4=R_6=R_{12}=R_{14}=R_{15}=R_{23}$=H, $R_{22}$ is OH, $R_3$ is —O-β-Gal$^2$-β-Glu, $R_5$=β-H, $C_{25}$ is S-configuration, $R_{27}$=—CH$_3$, X is O, Z is -β-Glu, Y is absent, and === is a single bond.

5. A method of claim 1, wherein $R_1=R_2=R_4=R_6=R_{12}=R_{14}=R_{15}=R_{23}$=H, $R_{22}$ is —$OCH_3$, $R_3$ is —O-β-$Gal^2$-β-Glu, $R_5$=β-H, $C_{25}$ is S-configuration, $R_{27}$=—$CH_3$, X is O, Z is -β-Glu, Y is absent, and === is a single bond.

6. A method of claim 1, wherein $R_1=R_2=R_4=R_6=R_{12}=R_{14}=R_{15}=R_{23}$=H, $R_3$ is

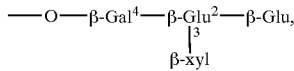

$R_5$=α-H, $R_{22}$ is absent, $R_{27}$=—$CH_3$, X=O, Y is a direct bond, Z is absent, === is a single bond, and C-25 is R-configuration.

7. A method of claim 1, wherein $R_1=R_2=R_4=R_6=R_{12}=R_{14}=R_{15}=R_{22}=R_{23}$=H, $R_3$ is

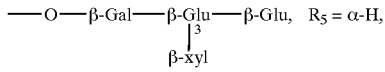

$R_{22}$ is absent, $R_{27}$=—$CH_3$, X=O, Y is a direct bond, Z is absent, === is a single bond, and C-25 is S-configuration.

8. A method of claim 1, wherein $R_1=R_4=R_6=R_{12}=R_{14}=R_{15}=R_{23}$=H, $R_2$=-α-OH, $R_3$ is

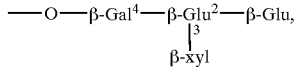

$R_5$=α-H, $R_{22}$ is absent, $R_{27}$=—$CH_3$, X=O, Y is a direct bond, === is a single bond, Z is absent, and C-25 is R-configuration.

9. A method of claim 1, wherein $R_1=R_4=R_6=R_{12}=R_{14}=R_{15}=R_{23}$=H, $R_2$=α-OH, $R_3$ is

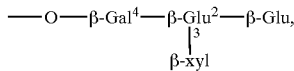

$R_5$=α-H, $R_{22}$ is absent, $R_{27}$=—$CH_3$, X=O, Y is a direct bond, === is a single bond, Z is absent, and C-25 is S-configuration.

10. A method of claim 1, wherein $R_1=R_2=R_4=R_6=R_{12}=R_{14}=R_{15}=R_{23}$=H, $R_3$ is

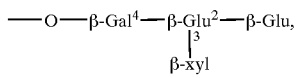

$R_{22}$ is absent, $R_{27}$=—$CH_3$, X=O, Y is a direct bond, Z is absent, C-25 is R-configuration, $R_5$ is absent, === at C5–6 is a double bond, and other === is a single bond.

11. A method of claim 1, wherein $R_1=R_2=R_4=R_6=R_{12}=R_{14}=R_{15}=R_{23}$=H, $R_5$ is absent, $R_{22}$ is absent, $R_{27}$=—$CH_3$, $R_3$ is

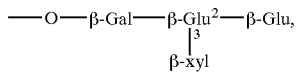

X=O, Y is a direct bond, Z is absent, C-25 is S-configuration, === at $C_{5-6}$ is a double bond, and other === is a single bond.

12. A method of claim 1, wherein $R_1=R_4=R_6=R_{12}=R_{14}=R_{15}=R_{23}$=H, $R_2$=-α-OH, $R_3$ is

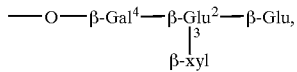

$R_{22}$ is absent, $R_{27}$=—$CH_3$, X=O, Y is a direct bond, Z is absent, C-25 is R-configuration, $R_5$ is absent, === at $C_{5-6}$ is a double bond, and other === is a single bond.

13. A method of claim 1, wherein $R_1=R_4=R_6=R_{12}=R_{14}=R_{15}=R_{23}$=H, $R_2$=-α-OH, $R_3$ is

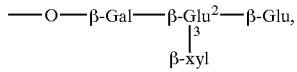

$R_{22}$ is absent, $R_{27}$=—$CH_3$, X=O, Y is a direct bond, Z is absent, C-25 is S-configuration, $R_5$ is absent, === at $C_{5-6}$ is a double bond, and other === is a single bond.

14. A method of claim 1, wherein said compound of Formula I is selected from the group consisting of:

- (25S)-26-0-β-D-glucopyranosyl-22-hydroxy-5β-furost-3β,26-diol-3-0-β-D-glucopyranosyl(1→2)-β-D-galactopyranoside;
- (25S)-26-0-β-D-glucopyranosyl-22-hydroxy-5β-furost-2β,3β,26-triol-3-0-β-D-glucopyranosyl(1→2)-β-D-galactopyranoside;
- (25R)-26-0-β-D-glucopyranosyl-22-hydroxy-5-ene-furost-3β,26-diol-3-0-α-L-rhamnopyranosyl(1→2)[β-D-glucopyranosyl(1→3)]-β-D-glucopyranoside;
- (25R)-26-0-β-D-glucopyranosyl-22-hydroxy-5-ene-furost-3β,26-diol-3-0-α-L-rhamnopyranosyl(1→2)[α-L-rhamnopyranosyl(1→4)]-β-D-glucopyranoside;
- (25R)-26-0-β-D-glucopyranosyl-22-hydroxy-5-ene-furost-3β,26-diol-3-0-β-D-galactopyranosyl(1→2)[β-D-galactopyranosyl(1→3)]-β-D-glucopyranoside;
- (25R)-26-0-β-D-glucopyranosyl-22-hydroxy-5-ene-furost-3β,26-diol-3-0-α-L-rhamnopyranosyl(1→2)-β-D-glucopyranoside; and
- (25S)-26-0-β-D-glucopyranosyl-5β-furost-20(22)-ene-3β,26-diol-3-0-β-D-glucopyranosyl(1→2)-β-D-galactopyranoside.

15. A method of claim 1, wherein the dementia is Alzheimer's disease, vascular dementia, or mixed type dementia.

* * * * *